US006831271B1

(12) United States Patent
Guevremont et al.

(10) Patent No.: US 6,831,271 B1
(45) Date of Patent: Dec. 14, 2004

(54) METHOD FOR SEPARATION AND ENRICHMENT OF ISOTOPES IN GASEOUS PHASE

(75) Inventors: Roger Guevremont, Gloucester (CA); Randy Purves, Gloucester (CA); David Barnett, Orleans (CA)

(73) Assignee: National Research Council Canada, Ottawa (CA)

( * ) Notice: Subject to any disclaimer, the term of this patent is extended or adjusted under 35 U.S.C. 154(b) by 0 days.

(21) Appl. No.: 09/762,238

(22) PCT Filed: Aug. 5, 1999

(86) PCT No.: PCT/CA99/00716

§ 371 (c)(1),
(2), (4) Date: May 9, 2001

(87) PCT Pub. No.: WO00/08456

PCT Pub. Date: Feb. 12, 2000

Related U.S. Application Data

(63) Continuation of application No. 09/321,820, filed on May 28, 1999, now Pat. No. 6,504,149.
(60) Provisional application No. 60/095,481, filed on Aug. 5, 1998.

(30) Foreign Application Priority Data

Jan. 29, 1999 (CA) .......................................... 2,260,572

(51) Int. Cl.[7] ............................................... H01J 49/40
(52) U.S. Cl. ....................................... 250/282; 250/281
(58) Field of Search ................................. 250/281, 282, 250/290, 292, 286, 288

(56) References Cited

U.S. PATENT DOCUMENTS

| 3,668,383 A | 6/1972 | Carroll |
| 4,855,595 A | 8/1989 | Blanchard |
| 5,420,424 A | 5/1995 | Carnahan et al. |

(List continued on next page.)

FOREIGN PATENT DOCUMENTS

| WO | WO 00/63949 A1 | 10/2000 |
| WO | WO 01/22049 A2 | 3/2001 |

OTHER PUBLICATIONS

Buryakov, I. A., Krylov, E. V., Nazarov, E. G., and Rasulev, U. K., A new method of separation of multi–atomic ions by mobility at atmospheric pressure using a high–frequency amplitude–symmetric strong electric field, Int. J. Mass Spectrom. Ion Processes, 128, 143 (1993).

(List continued on next page.)

*Primary Examiner*—John D. Lee
*Assistant Examiner*—Paul M. Gurzo
(74) *Attorney, Agent, or Firm*—Freedman & Associates

(57) ABSTRACT

The present invention relates to a method for separating and enriching stable isotopes in gas phase using the principles of high field asymmetric waveform ion mobility spectrometry, substantially at atmospheric pressure (760 torr) and substantially at room temperature (298 K). Specifically, the method of the present invention may be used to separate and enrich isotopes of chlorine. Electrospray ionization may be used to generate a gaseous mixture of ions and the ion beam exiting the high field asymmetric waveform ion mobility spectrometer may be sampled into a mass spectrometer for isotope identification.

17 Claims, 17 Drawing Sheets

U.S. PATENT DOCUMENTS

| | | | |
|---|---|---|---|
| 5,723,861 A | | 3/1998 | Carnahan et al. |
| 5,736,739 A | | 4/1998 | Uber et al. |
| 5,763,876 A | * | 6/1998 | Pertinarides et al. ........ 250/288 |
| 5,789,745 A | | 8/1998 | Martin et al. |
| 5,801,379 A | | 9/1998 | Kouznetsov |
| 5,869,831 A | | 2/1999 | De La Mora et al. |
| 5,905,258 A | | 5/1999 | Clemmer et al. |
| 6,041,734 A | | 3/2000 | Raoux et al. |
| 6,162,709 A | | 12/2000 | Raoux et al. |
| 6,323,482 B1 | | 11/2001 | Clemmer et al. |
| 6,512,224 B1 | * | 1/2003 | Miller et al. ................ 250/286 |
| 2001/0030285 A1 | | 10/2001 | Miller et al. |
| 2001/0032929 A1 | | 10/2001 | Fuhrer et al. |
| 2001/0032930 A1 | | 10/2001 | Gillig et al. |
| 2002/0070338 A1 | | 6/2002 | Loboda |
| 2002/0070339 A1 | | 6/2002 | Clemmer |

OTHER PUBLICATIONS

Krylov, E. V., A method of reducing diffusion losses in a drift spectrometer, Tech. Phys., 44, 113 (1999).

Carnahan, B., Day, S., Kouznetsov, V., Matyjaszczyk, M., and Tarassov, A., Filed Ion Spectrometry—A New Analytical Technology for Trace Gas Analysis Proceedings of the 41st Annual ISA Analysis Division Symposium, , Framingham, MA, pp. 85 (1996).

Riegner, D. E., Harden, C. S., Carnahan, B., and Day, S., Qualitative Evaluation of Field Ion Spectrometry for Chemical Warfare Agent Detection Proceedings of the 45th ASMS Conference on Mass Spectrometry and Allied Topics, , Palm Springs, California, pp. 473 (1997).

Spangler, G. E., Fundamental considerations for the application of miniature ion mobility spectrometry to field analytical applications, Field Analytical Chemistry and Technology, 4, 255 (2000).

Eiceman, G. A., Nazarov, E. G., Tadjikov, B., and Miller, R. A., Monitoring volatile organic compounds in ambient air inside and outside buildings with the use of a radio–frequency–based ion–mobility analyzer with a micromachined drift tube, Field Anal. Chem. Tech., 4, 297 (2000).

Miller, R. A., Eiceman, G. A., Nazarov, E. G., and King, A. T., A novel micromachined high–field asymmetric waveform–ion mobility spectrometer, Sensors Actuators B Chem. 67, 300 (2000).

Spangler, G. E., and Miller, R. A., Application of mobility theory to the interpretation of data generated by linear and RF excited ion mobility spectrometers, Int. J. Mass Spectrom., 214, 95–104 (2002).

Kiai, S. M. S., Confinement of ions in a radio frequency quadrople ion trap supplied with a periodic impulsional potential, Int. J. Mass Spectrom., 188, 177 (1999).

Kiai, S. M. S., Andre, J., Zerega, Y., Brincourt, G., and Catella, R., Study of a Quadrupole Ion Trap Supplied with a Periodic Impulsional Potential, Int. J Mass Spectrom. and Ion Processes, 107, 191 (1991).

Whetten, N. R., Macroscopic particle motion in quadrupole fields, J. Vac. Sci. Technol., 11, 515 (1974).

Buryakov, I. A., Kolomiets, Y. N., and Luppu, B. V., Detection of Explosive Vapors in the Air Using an Ion Drift Nonlinearity Spectrometer, J. Anal. Chem., 56, 336 (2001).

Krylov, E. V., Pulses of Special Shapes Formed on a Capacitive Load, Instruments and Experimental Techniques, 40, 628 (1997).

* cited by examiner

Table 1   List of Prominent Ions Observed in Figure 10B.

| m/z | background ion | m/z | background ion |
|---|---|---|---|
| -43 | $CH_3CO^-$ | -97 | $HSO_4^-$ |
| -45 | $HCO_2^-$ | -123 | $[H_2(EDTA)-(CO_2)]^{2-}$ |
| -59 | $CH_3COO^-$ | -125 | $H(NO_3)_2^-, H_2C_2O_4{}^{35}Cl^-$ |
| -62 | $NO_3^-$ | -127 | $H_2C_2O_4{}^{37}Cl^-$ |
| -71,73,75 | $HCl_2^-$ | -145 | $H_2(EDTA)^{2-}$ |
| -75 | $CH_3O(CO_2)^-$ | -156 | $Na(HEDTA)^{2-}$ |
| -79, 81 | $Br^-$ | -164 | $K(HEDTA)^{2-}$ |
| -81, -83 | $(H_2CO_3)Cl^-$ | -291 | $H_3(EDTA)^-$ |
| -89 | $H_2C_2O_4^-$ | | |

FIG. 10C

METHOD FOR SEPARATION AND ENRICHMENT OF ISOTOPES IN GASEOUS PHASE

This application is a continuation of U.S. patent application Ser. No. 09/321,820 filed May 28, 1999 now issued as U.S. Pat. No. 6,504,149 on Jan. 7, 2003 which claims the benefit of U.S. Provisional Application No. 60/095,481 filed Aug. 5, 1998.

FIELD OF THE INVENTION

The present invention relates to a method for separating and enriching isotopes in gaseous phase based on the principle of high field asymmetric waveform ion mobility spectrometry.

BACKGROUND OF THE INVENTION

High sensitivity and amenability to miniaturization for field-portable applications have helped to make ion mobility spectrometry an important technique for the detection of many compounds, including narcotics, explosives, and chemical warfare agents (see, for example, G. Eiceman and Z. Karpas, *Ion Mobility Spectrometry* (CRC. Boca Raton, Fla. 1994); and *Plasma Chromatography*, edited by T. W. Carr (Plenum, New York, 1984)). In ion mobility spectrometry, gas-phase ion mobilities are determined using a drift tube with a constant electric field. Ions are gated into the drift tube and are subsequently separated based upon differences in their drift velocity. The ion drift velocity is proportional to the electric field strength at low electric fields (e.g., 200 V/cm) and the mobility, K, which is determined from experimentation, is independent of the applied field. At high electric fields (e.g. 5000 or 10000 V/cm), the ion drift velocity may no longer be directly proportional to the applied field, and K becomes dependent upon the applied electric field (see G. Eiceman and Z. Karpas, *Ion Mobility Spectrometry* (CRC. Boca Raton, Fla. 1994); and E. A. Mason and E. W. McDaniel, *Transport Properties of Ions in Gases* (Wiley, New York, 1988)). At high electric fields, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry (see I. Buryakov, E. Krylov, E. Nazarov, and U. Rasulev, Int. J. Mass Spectrom. Ion Proc. 128. 143 (1993); D. Riegner, C. Harden, B. Carnahan, and S. Day, Proceedings of the 45th ASMS Conference on Mass Spectrometry and Allied Topics, Palm Springs, Calif., 1–5 Jun. 1997, p. 473; B. Carnahan, S. Day, V. Kouznetsov, M. Matyjaszczyk, and A. Tarassov, Proceedings of the 41st ISA Analysis Division Symposium, Framingham, Mass., 21–24 Apr. 1996, p. 85; and B. Carnahan and A. Tarassov, U.S. Pat. No. 5,420,424). Ions are separated in FAIMS on the basis of the difference in the mobility of an ion at high field $K_h$ relative to its mobility at low field K. That is, the ions are separated because of the compound dependent behaviour of $K_h$ as a function of the electric field. This offers a new tool for atmospheric pressure gas-phase ion studies since it is the change in ion mobility and not the absolute ion mobility that is being monitored.

An instrument based on the FAIMS concept has been designed and built by Mine Safety Appliances Company of Pittsburgh, Pa. ("MSA") for use in trace gas analysis. The MSA instrument is described in U.S. Pat. No. 5,420,424 and is available under the trade mark FIS (for Field Ion Spectrometer). While the use of the MSA instrument (and similar Instruments based on the FAIMS concept) for trace gas analysis is known, the inventors believe that they have identified certain heretofore unrealized properties of these instruments which make them more versatile. Based this realization the inventors have developed what is believed to be a previously unknown method for separation of isotopes of ions. A summary and detailed description of the present invention is provided below.

SUMMARY OF THE INVENTION

The present invention provides a method for identifying isotopes, comprising the steps of:
a) providing at least one ionization source for providing ions at least some of which are isotopes;
b) providing an analyzer region defined by a space between at least first and second spaced apart electrodes, said analyzer region being in communication with at least one of each of a gas inlet, a gas outlet, an ion inlet and an ion outlet, and introducing said ions into said analyzer region through said ion inlet;
c) applying an asymmetric waveform voltage and a direct current compensation voltage to at least one of said electrodes;
d) setting said asymmetric waveform voltage;
e) varying said direct current compensation voltage and measuring resulting transmitted ions at said ion outlet, so as to produce a compensation voltage scan for said transmitted ions;
f) identifying peaks in said compensation voltage scan corresponding to said isotopes; and
g) setting said direct current compensation voltage to correspond to one of said peaks, so as to separate and enrich a desired isotope.

Advantageously, the method is operable substantially at atmospheric pressure and substantially at room temperature.

The method may further include the step of detecting said transmitted ions by mass spectrometry.

Such transmitted ions may be subjected to a mass analysis scan to provide ion intensity data over a selected range of mass to charge ratios.

Typically, the method includes providing a gas flow through said analyzer region, so as to transport said ions along said analyzer region, although it will be understood that other ion transport means are possible.

Furthermore, in identifying a peak, it will be understood that the term peak is not limited to the apex of the peak, and at a peak will typically have a noticeable width, or a compensation voltage range in which the peak appears.

Finally, it will be understood that while mass spectrometry may be used for the purpose of compensation voltage scans, mass spectrometry is not necessary once the operating conditions have been determined. That is to say, isotopes separated and enriched by the above method may be collected for further processing.

BRIEF DESCRIPTION OF THE DRAWINGS

For a better understanding of the present invention, and by way of example, reference will now be made to the accompanying drawings, which show preferred embodiments of the present invention in which:

FIG. 10C shows a table of the major ions in an electrospray ionization mass spectrometry (ESI-MS) spectrum for the sample solution used in FIG. 9;

DETAILED DESCRIPTION OF THE INVENTION

As an important preliminary note, the discussion below generally uses the term "ion" to mean a charged atomic or molecular entity, the "ion" can be any electrically charged particle, solid, liquid or gas, of any size. The discussion below refers to both positively charged and negatively charged ions, and it will be understood by a person skilled in the art that, for any individual analysis, only one of these types of ions will be used.

The discussion below also generally uses the term "isotopes" to mean members of a chemical-element family that have two or more nuclides with the same number of protons but different numbers of neutrons, such that they differ in atomic mass but have the same chemical attributes.

The disclosure also uses the term "ion selected compensation voltage" (IS-CV) spectra which refers to scanning the compensation voltage applied to a FAIMS analyzer, as discussed below, typically while monitoring a single mass-to-charge (m/z) value. The term "total ion current compensation voltage" (TIC-CV) spectra is also used to refer to a compensation voltage scan which shows the sum of a signal for all detected ions in a given m/z range.

Principles of FAIMS

The principles of operation of FAIMS have been described in Buryakov et. al. (see I. Buryakov, E. Krylov, E. Nazarov, and U. Rasulev, Int. J. Mass Spectrom. Ion Proc. 128. 143 (1993)) and are summarized here briefly. The mobility of a given ion under the influence of an electric field can be expressed by: $K_h(E)=K(1+f(E))$, where $K_h$ is the mobility of an ion at high field, K is the coefficient of ion mobility at low electric field and "f(E)" describes the functional dependence of the ion mobility on the electric field (see E. A. Mason and E. W. McDaniel, *Transport Properties of Ions in Gases* (Wiley, New York, 1988); and I. Buryakov, E. Krylov, E. Nazarov, and U. Rasulev, Int. J. Mass Spectrom. Ion Proc. 128. 143 (1993)).

Figure 1:
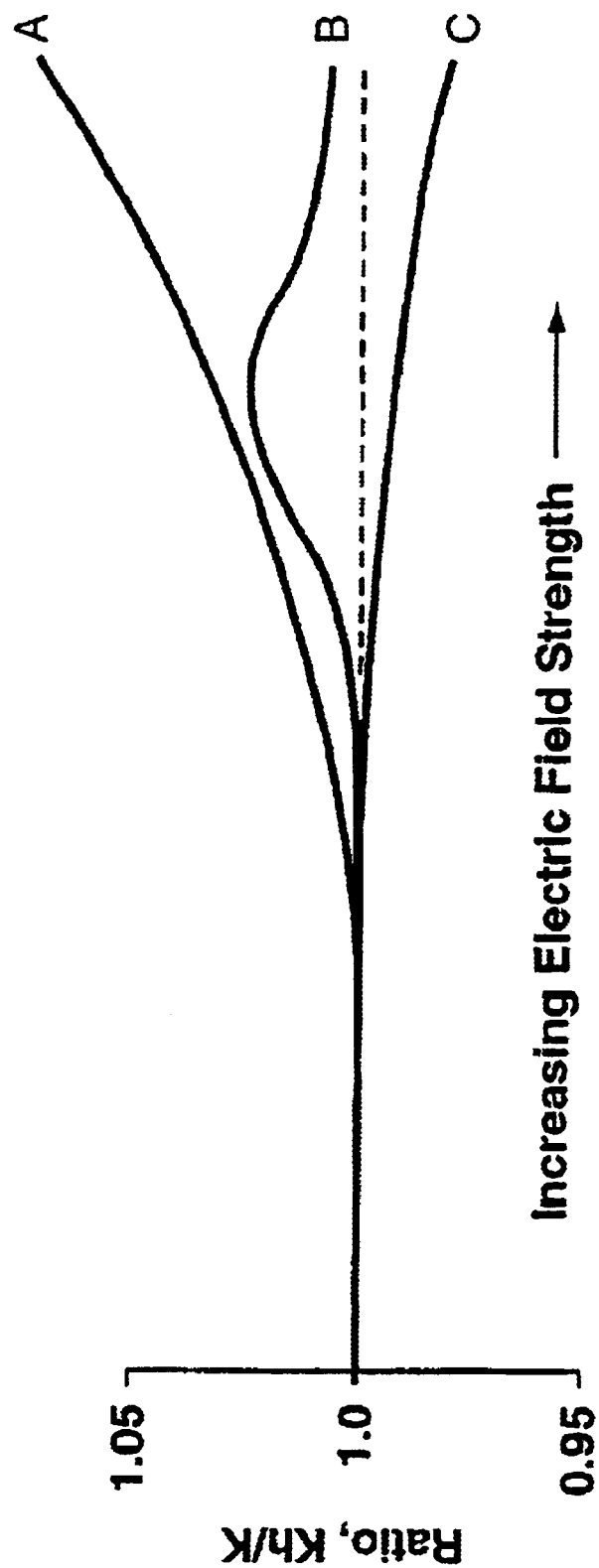
FIG. 1 shows three possible examples of changes in ion mobility as a function of the strength of an electric field.
Figure 2:
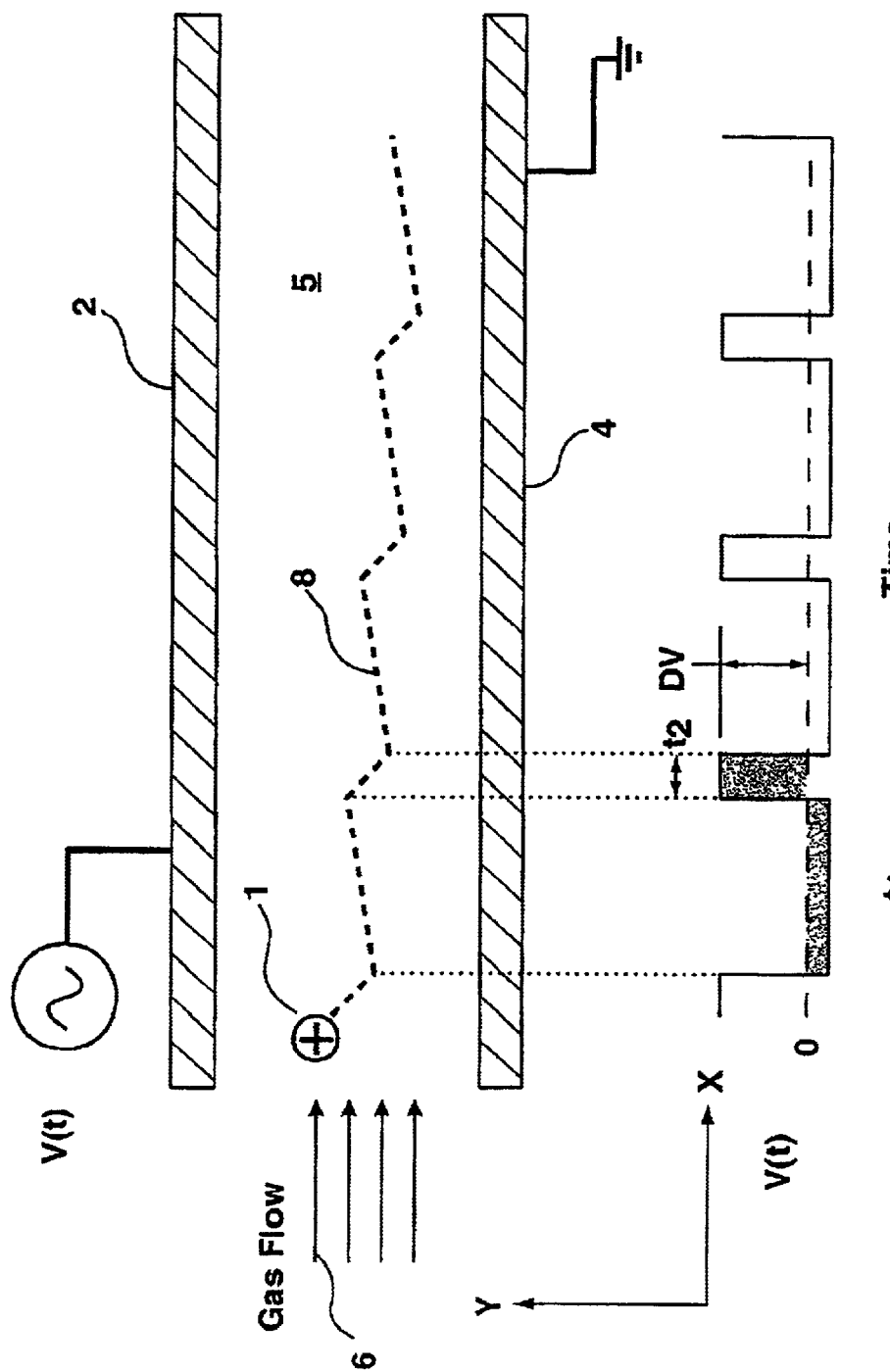
FIG. 2 illustrates the trajectory of an ion between two parallel plate electrodes under the influence of the electrical potential V(t)

Referring to FIG. 1, three examples of changes in ion mobility as a function of the strength of an electric field are shown: the mobility of type A ions increases with increasing electric field strength; the mobility of type C ions decreases; and the mobility of type B ions increases initially before decreasing at yet higher fields. The separation of ions in FAIMS is based upon these changes in mobility at high electric fields. Consider an ion 1, for example a type A ion shown in FIG. 1, that is being carried by a gas stream 6 between two spaced apart parallel plate electrodes 2, 4 as shown in FIG. 2. The space between the plates 2, 4 defines an analyzer region 5 in which the separation of ions may take place. The net motion of the ion 1 between the plates 2, 4 is the sum of a horizontal x-axis component due to a flowing stream of gas 6 and a transverse y-axis component due to the electric field between the plates 2, 4. (The term "net" motion refers to the overall translation that the ion 1 experiences, even when this translational motion has a more rapid oscillation superimposed upon it.) One of the plates is maintained at ground potential (here, the lower plate 4) while the other (here, the upper plate 2) has an asymmetric waveform, V(t), applied to it. The asymmetric waveform V(t) is composed of a high voltage component, $V_1$, lasting for a short period of time $t_2$ and a lower voltage component, $V_2$, of opposite polarity, lasting a longer period of time $t_1$.

The waveform is synthesized such that the integrated voltage-time product (thus the field-time product) applied to the plate during a complete cycle of the waveform is zero (i.e., $V_1 t_2 + V_2 t_1 = 0$); for example +2000 V for 10 μs followed by −1000 V for 20 μs. FIG. 2 illustrates the ion trajectory 8 (as a dashed line) for a portion of the waveform shown as V(t). The peak voltage during the shorter, high voltage portion of the waveform will be called the "dispersion voltage" or DV in this disclosure. During the high voltage portion of the waveform, the electric field will cause the ion 1 to move with a transverse velocity component $v_1 = K_h E_{high}$, where $E_{high}$ is the applied field, and $K_h$ is the high field mobility under ambient electric field, pressure and temperature conditions. The distance travelled will be $d_1 = v_1 t_2 = K_h E_{high} t_2$, where $t_2$ is the time period of the applied high voltage. During the longer duration, opposite polarity, low voltage portion of the waveform, the velocity component of the ion will be $v_2 = K E_{low}$, where K is the low field ion mobility under ambient pressure and temperature conditions. The distance travelled is $d_2 = v_2 t_1 = K E_{low} t_1$. Since the asymmetric waveform ensures that $(V_1 t_2) + (V_2 t_1) = 0$, the field-time products $E_{high} t_2$ and $E_{low} t_1$ are equal in magnitude. Thus, if $K_h$ and K are identical, $d_1$ and $d_2$ are equal, and the ion 1 will be returned to its original position along the y-axis during the negative cycle of the waveform (as would be expected if both portions of the waveform were low voltage). If at $E_{high}$ the mobility $K_h > K$, the ion 1 will experience a net displacement from its original position relative to the y-axis. For example, positive ions of the type A shown in FIG. 1 will travel further during the positive portion of the waveform (i.e., $d_1 > d_2$) and the type A ion 1 will migrate away from the upper plate 2 (as illustrated by the dashed line 8 in FIG. 2). Similarly, ions of type C will migrate towards the upper plate 2.

If an ion of type A is migrating away from the upper plate 2, a constant negative dc voltage can be applied to this plate 2 to reverse, or "compensate" for this transverse drift. This dc voltage, called the "compensation voltage" or CV in this disclosure, prevents the ion 1 from migrating towards either plate 2, 4. If ions derived from two compounds respond differently to the applied high electric fields, the ratio of $K_h$ to K may be different for each compound. Consequently, the magnitude of the compensation voltage CV necessary to prevent the drift of the ion toward either plate 2, 4 may also be different for each compound. Under conditions in which the compensation voltage CV is appropriate for transmission of one compound, the other will drift towards one of the plates 2, 4 and subsequently be lost. The speed at which the compound will move to the wall of the plates 2, 4 depends on the degree to which its high field mobility properties differ from those of the compound that will be allowed to pass under the selected condition. A FAIMS instrument or apparatus is an ion filter capable of selective transmission of only those ions with the appropriate ratio of $K_h$ to K.

The term FAIMS, as used in this disclosure, refers to any device which can separate ions via the above described mechanism, whether or not the device has focusing or trapping behaviour.

Improvements to FAIMS

The FAIMS concept was first shown by Buryakov et. al. using flat plates as described above. Later, Carnahan et. al. improved the sensor design by replacing the flat plates used to separate the ions with concentric cylinders (see B. Carnahan, S. Day, V. Kouznetsov, M. Matyjaszczyk, and A. Tarassov, Proceedings of the 41st ISA Analysis Division Symposium, Framingham, Mass., 21–24 Apr. 1996, p. 85; U.S. Pat. No. 5,420,424 issued to Carnahan et al.). The concentric cylinder design has several advantages including higher sensitivity than the flat plate configuration (see R. W. Purves, R. Guevremont, S. Day, C. W. Pipich, and M. S. Matyjaszczyk, Rev. Sci. Instrum., 69, 4094 (1998)).

As mentioned earlier, an instrument based on the FAIMS concept has been built by Mine Safety Appliances Company (MSA). The MSA instrument uses the concentric cylinder design and is described further below. (For the purposes of this disclosure, the MSA instrument is referred to as FAIMS-E, where E refers to an electrometer or electric current detection device.)

One previous limitation of the cylindrical FAIMS technology (see D. Riegner, C. Harden, B. Carnahan, and S. Day, Proceedings of the 45th ASMS Conference on Mass Spectrometry and Allied Topics, Palm Springs, Calif., 1–5 Jun. 1997, p. 473; and B. Carnahan, S. Day, V. Kouznetsov, M. Matyjaszczyk, and A. Tarassov, Proceedings of the 41st ISA Analysis Division Symposium, Framingham, Mass., 21–24 Apr. 1996, p. 85) was that the identity of the peaks appearing in the FAIM-E CV spectra could not be unambiguously confirmed due to the unpredictable changes in $K_h$ at high electric fields.

Thus, one way to extend the capability of instruments based on the FAIMS concept, such as the FAIMS-E instrument, is to provide a way to determine the make-up of the PAIMS-E CV spectra more accurately, for example, by introducing ions from the FAIMS-E device into a mass spectrometer for mass-to-charge (m/z) analysis.

In addition, it has been found that a modified FAIMS instrument, or any similar instrument, can be used in a new method of separating isotopes of gaseous phase ions. The present invention is directed to a new method of separating isotopes of ions and illustrates the method by an example. Details of the method of the present invention are described below.

Electrospray Ionization

ESI is one of several related techniques that involves the transfer of ions (which can be either positively or negatively charged) from liquid phase into the gas-phase. Kebarle has described four major processes that occur in electrospray ionization (intended for use in mass spectrometry): (1) production of charged droplets, (2) shrinkage of charged droplets by evaporation, (3) droplet disintegration (fission), and (4) formation of gas-phase ions (Kebarle, P. and Tang, L. Analytical Chemistry, 65 (1993) pp. 972A–986A). In ESI, a liquid solution (e.g. 50/50 w/w water/methanol) is passed through a metal capillary (e.g., 200 $\mu$m outer diameter and 100 $\mu$m ID) which is maintained at a high voltage to generate the charged droplets, say +2000 V (50 nA) for example. The liquid samples can be pumped through at, say, 1 $\mu$L/min. The high voltage creates a very strong, non-constant electric field at the exit end of the capillary, which nebulizes the liquid exiting from the capillary into small charged droplets and electrically charged ions by mechanisms described by Kebarle and many others. Several related methods also exist for creating gas-phase ions from solution phase. Some examples of these methods include ionspray, which uses mechanical energy from a high velocity gas to assist in nebulization; thermospray, which applies heat instead of a voltage to the capillary; and nanospray, which uses small ID capillaries. In this disclosure, the term ESI is used to encompass any technique that creates gas-phase ions from solution.

Modified FAIMS-E

As a first step, the FAIMS-E device designed and built by Mine Safety Appliances Company was modified to permit the introduction of ions using ESI. The inventors believe that the coupling of an ESI source together with a FAIMS-E device is not obvious as it is known that ions produced by ESI have a high degree of solvation, and that a FAIMS-E device may not function properly when exposed to high levels of solvent vapour. The inventors have developed various practical embodiments of an apparatus that combines an ESI source together with a FAIMS device to show that such coupling is possible.

Figure 3A:
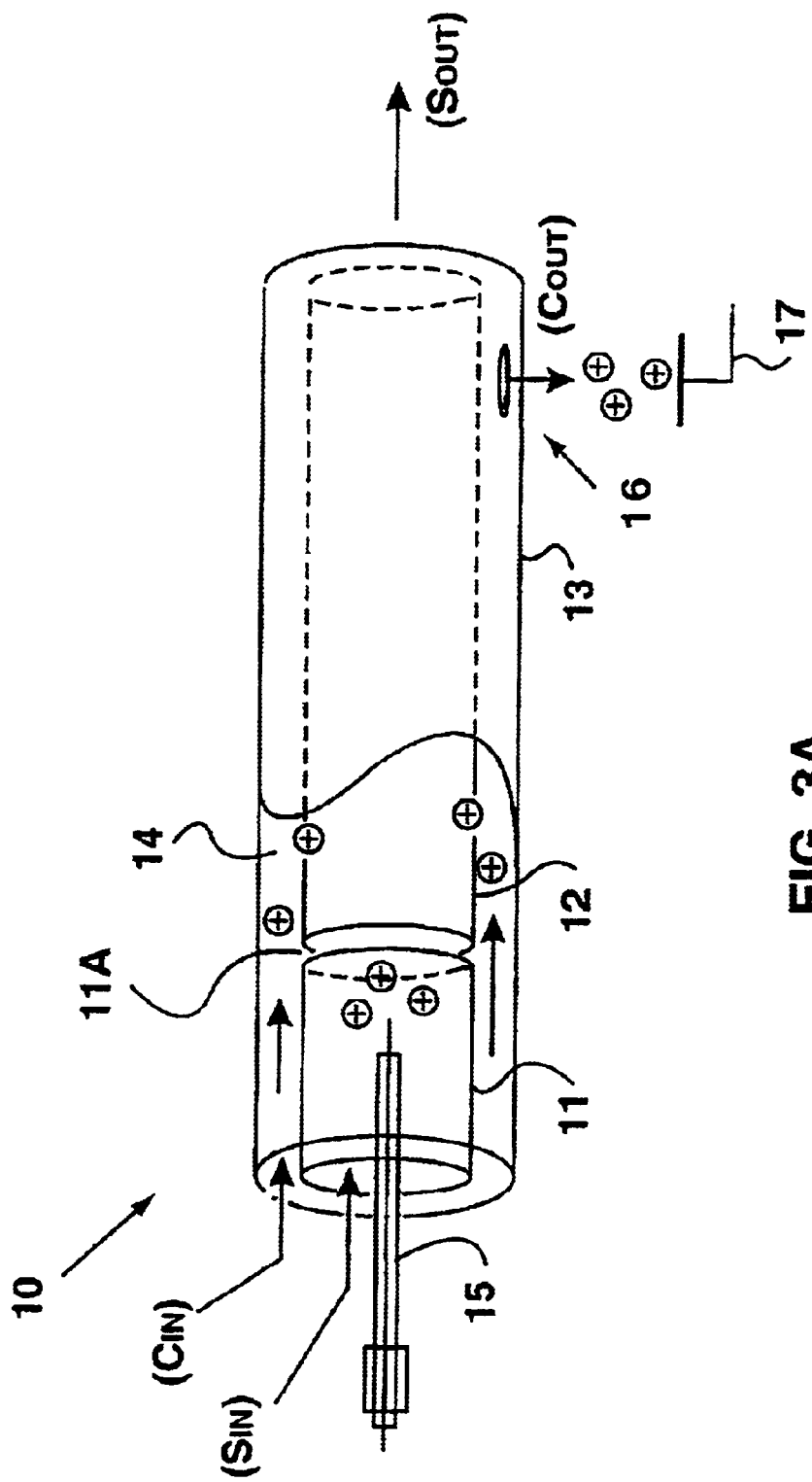
FIGS. 3A and 3B show schematically an embodiment of a modified FAIMS device.
Figure 3B:
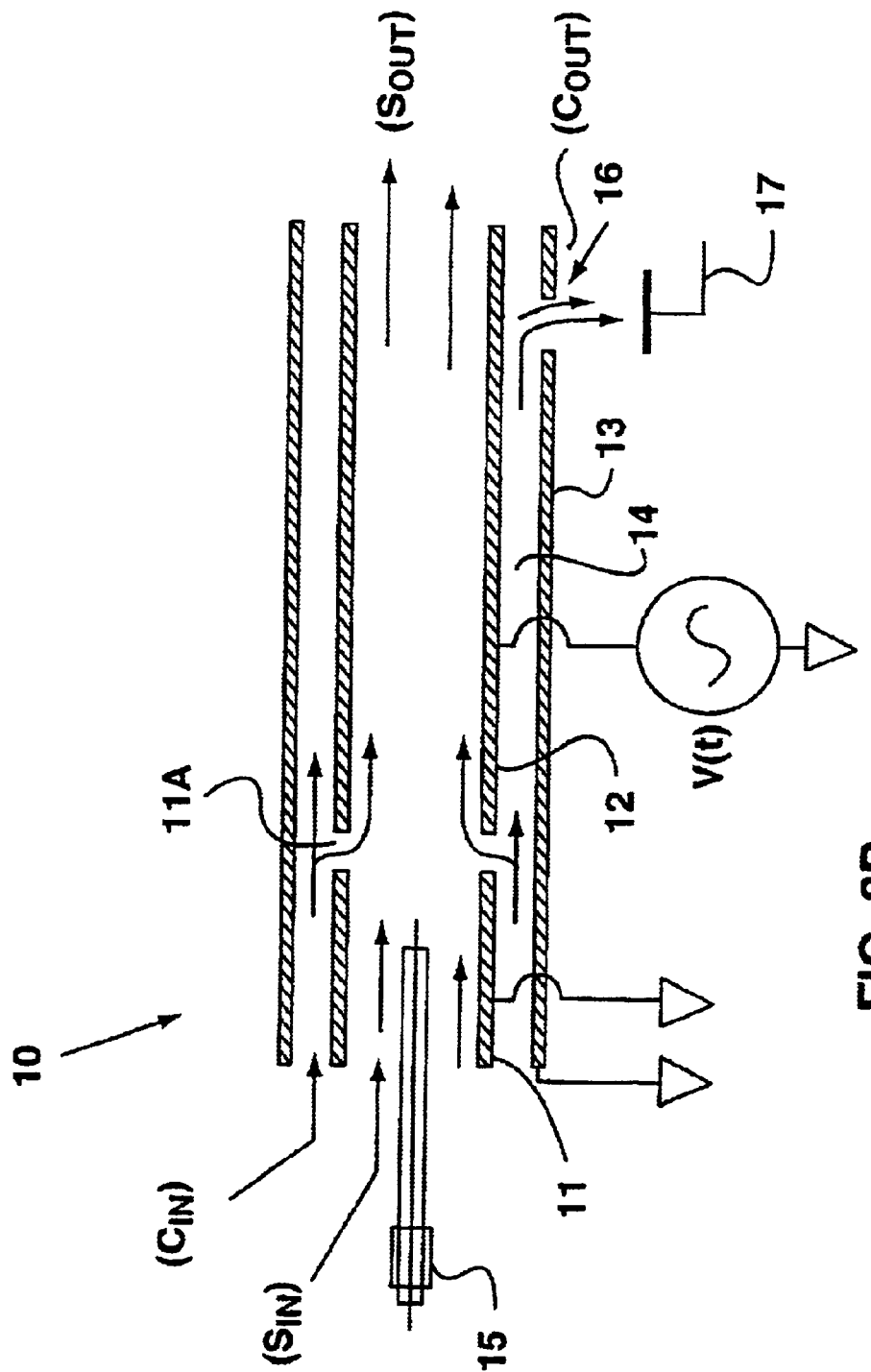

One example is the modified FAIMS-E device 10 shown schematically in 3-dimensional view in FIG. 3A and in cross section in FIG. 3B. The FAIMS-E apparatus 10 is composed of two short inner cylinders or tubes 11, 12 which are axially aligned and positioned about 5 mm apart, and a long outer cylinder 13 which surrounds the two inner cylinders 11, 12. The inner cylinders 11, 12 (12 mm inner diameter, 14 mm outer diameter), are about 30 mm and 90 mm long, respectively, while the outer cylinder 13 (18 mm inner diameter, 20 mm outer diameter) is about 125 mm long. Ion separation takes place in the 2 mm annular space of FAIMS analyzer region 14 between the long inner cylinder 12 and the outer cylinder 13. To produce ions using electrospray ionization (ESI), for introduction into the FAIMS analyzer region 14 of the FAIMS device, the metal capillary of the ESI needle 15 was placed along the central axis of the shorter inner cylinder 11, terminating about 5 mm short of the gap or ion inlet between the two inner cylinders 11, 12. The positioning of the ESI needle 15 shown in FIGS. 3(A) and 3(B) differs from the positioning of the ionization source found in the MSA FAIMS-E device in that the ESI needle 15 does not extend through the long inner cylinder 12 to which the asymmetric waveform V(t) is typically applied. By introducing the ESI needle 15 from the opposite end of the FAIMS-E, i.e. through the short inner cylinder 11, and not positioning the tip of the ESI needle 15 too close to the long inner cylinder 12, the performance of the ESI needle 15 is not compromised by the asymmetric waveform V(t), which would be the case if the ESI needle 15 was positioned within the long inner cylinder 12 (as disclosed in U.S. Pat. No. 5,420,424).

As explained above, the FAIMS-E device 10 can be considered as an ion "filter", with the capability of selectively transmitting one type of ion out of a mixture. If a mixture of ions is presented continuously to the entrance of the FAIMS analyzer region 14, for example by an ESI needle 15, and the ions are carried along the length of the analyzer 14 by a flowing gas under conditions in which no voltages are applied to either the inner cylinder 12 or outer cylinder 13 (i.e. the electrodes are grounded), some finite level of transmission for every ion is expected, albeit without any separation.

It might be expected that the detected current of any selected ion in this mixture should never exceed the current for that ion when it is transmitted through the device 10 in the no-voltages condition. It might also be expected that application of high voltages (i.e. application of transverse fields, perpendicular to the gas flows) designed to yield ion separation should not increase the ion transmission, but should decrease transmission through collisions with the walls of the cylinders 12, 13. That is, the asymmetric waveform might effectively narrow the "width" of the FAIMS analyzer region 14, and therefore should decrease the ion transmission. However, contrary to this prediction, experiments conducted by the inventors and described in this disclosure have shown that the sensitivity of ion detection in the cylindrical geometry FAIMS-E 10 increases as the voltage amplitude of the asymmetric waveform V(t) is increased. As will be explained below, these unusual observations suggest that atmospheric pressure ion focusing is occurring in the FAIMS analyzer region 14.

Still referring to FIGS. 3A and 3B, four gas connections to the FAIMS-E apparatus 10 are shown. Compressed gas (e.g. air or nitrogen) is passed through a charcoal/molecular sieve gas purification cylinder (not shown) into the FAIMS-E 10 through carrier in ($C_{in}$) and/or sample in ($S_{in}$) ports. The gas exits the FAIMS-E 10 via the carrier out ($C_{out}$) and/or sample out ($S_{out}$) ports. All four gas flow rates can be adjusted. Non-volatile analytes are typically introduced into the FAIMS-E 10 using an ESI needle 15. Alternatively, volatile analytes may be introduced into the FAIMS-E 10 through the $S_{in}$ line, and a portion may be ionized as the compound(s) pass by a corona discharge needle.

Still referring to FIGS. 3A and 3B, the outer cylinder 13 of the FAIMS-E apparatus 10, and the shorter inner cylinder 11, are typically held at an adjustable electrical potential ($V_{FAIMS}$). $V_{FAIMS}$ is usually ground potential in FAIMS-E. During operation, a high frequency high voltage asymmetric waveform is applied to the long inner cylinder 12 to establish the electric fields between the inner and outer cylinders 12, 13. In addition to this high frequency (e.g., 210 kHz) high voltage waveform a dc offset voltage (i.e. the compensation voltage CV added to FAIMS) is applied to the long inner cylinder 12. This leads to the separation of ions in the FAIMS analyzer region 14 in the manner discussed earlier.

Still referring to FIGS. 3A and 3B, some of the ions produced by the ionization source are carried by the gas stream along the length of the annular space between the outer cylinder 13 and the long inner cylinder 12, also referred to as the FAIMS analyzer region 14. If the combination of DV and CV are appropriate, and the ion is not lost to the tube walls, a series of openings or ion outlets 16 near the downstream end of the outer cylinder 13 allow the ions to be extracted to an electrical current detector 17 which is biased to about −100 V. (Note that here the carrier gas also exits from the ion outlet 16.)

Figure 4:
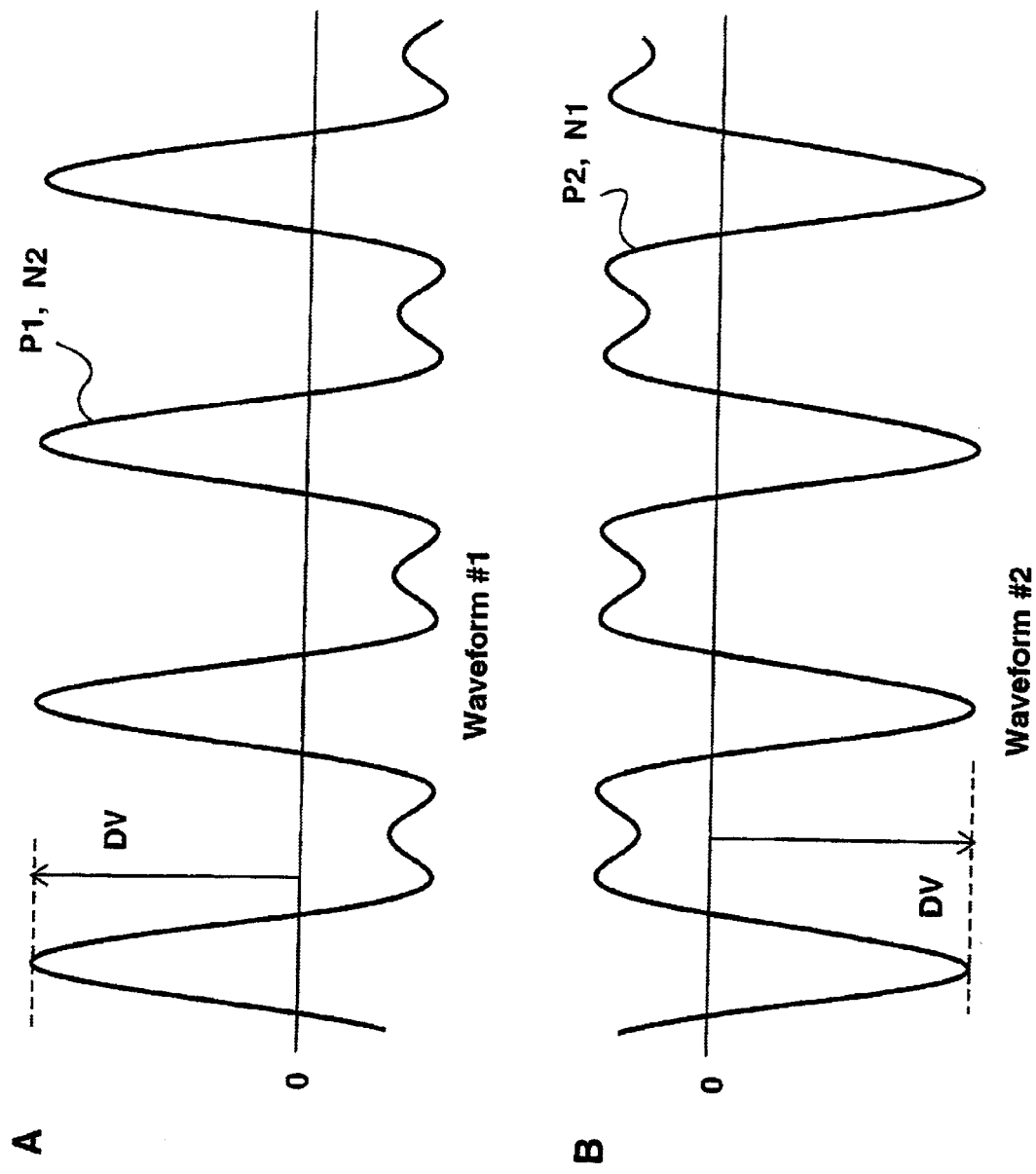
FIG. 4 illustrates two opposite waveform modes which may be used with the apparatus of FIGS. 3A and 3B.

In practice, the simplified square wave version of V(t) shown in FIG. 2 cannot be used because of the electrical power demands that such a wave would place on the waveform generator. The actual waveforms V(t) appear in FIG. 4. These waveforms are produced by the electronic addition of a sine wave and its harmonic of twice the frequency. As shown in FIG. 4, the FAIMS-E apparatus 10 operates using one of the two waveform modes (with the waveform applied to the inner cylinder). These reversed polarity waveform modes do not yield "reversed polarity" CV spectra as might be expected. This is because the reversal of polarity in this manner also creates a mirror image effect of the ion focusing behaviour of FAIMS. The result of such polarity reversal is that the ions are not focussed, but rather collide with the walls of the cylinders 12, 13. The mirror image of a focusing valley is a hill-shaped potential surface. (This characteristic, and the various "modes" of operation of FAIMS, is discussed further below.)

FAIMS-MS

As discussed earlier, one way to extend the functionality of FAIMS devices is to couple them together with a mass spectrometer. The use of a mass spectrometer together with a FAIMS device is advantageous because the mass spectrometer facilitates a mass-to-charge (m/z) analysis to determine the make-up of CV spectra more accurately. One possible FAIMS-MS embodiment is described here.

Figure 5A:
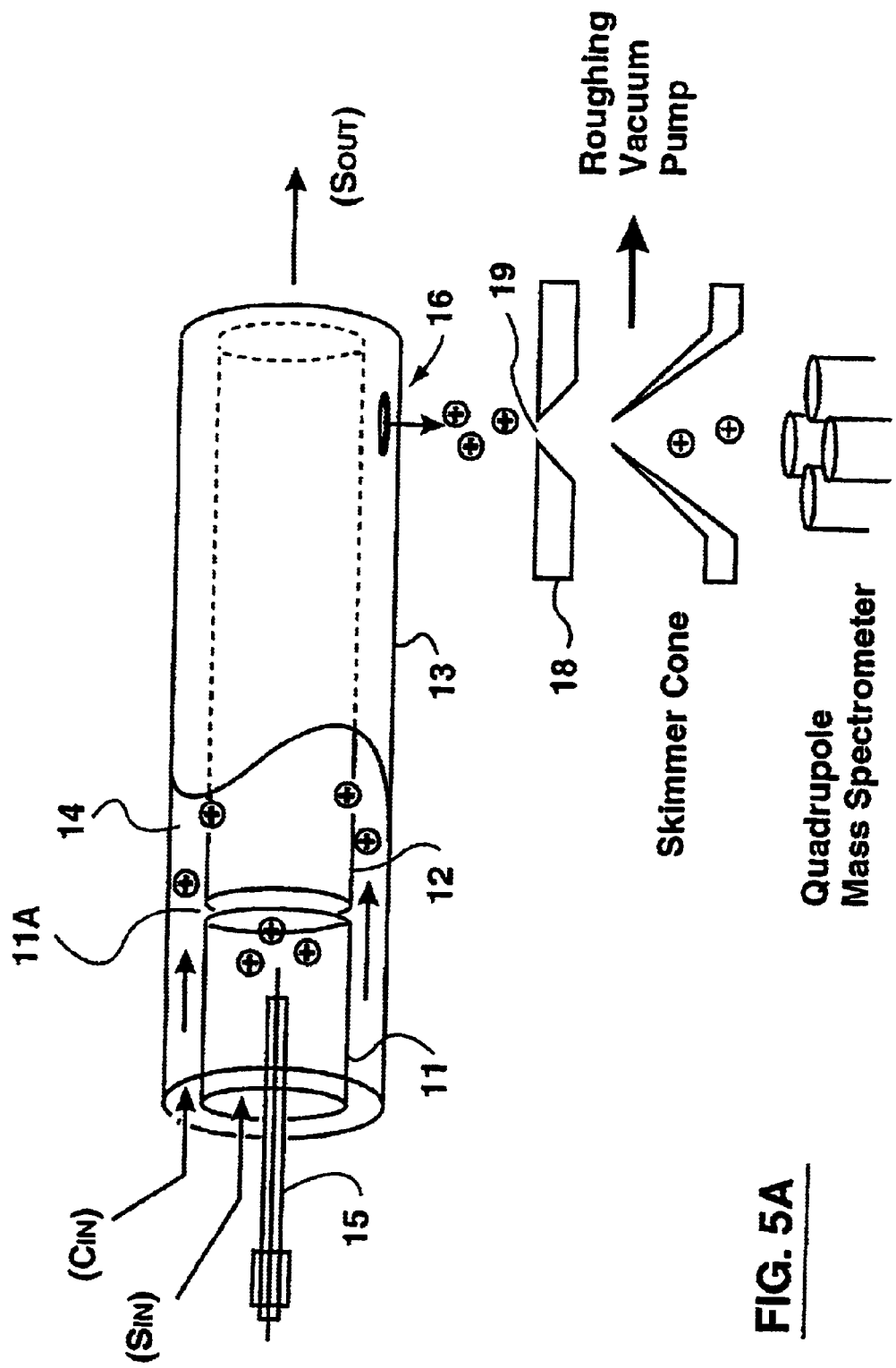
FIGS. 5A and 5B show schematically the coupling of the FAIMS apparatus of FIGS. 3A and 3B together with a mass spectrometer.
Figure 5B:
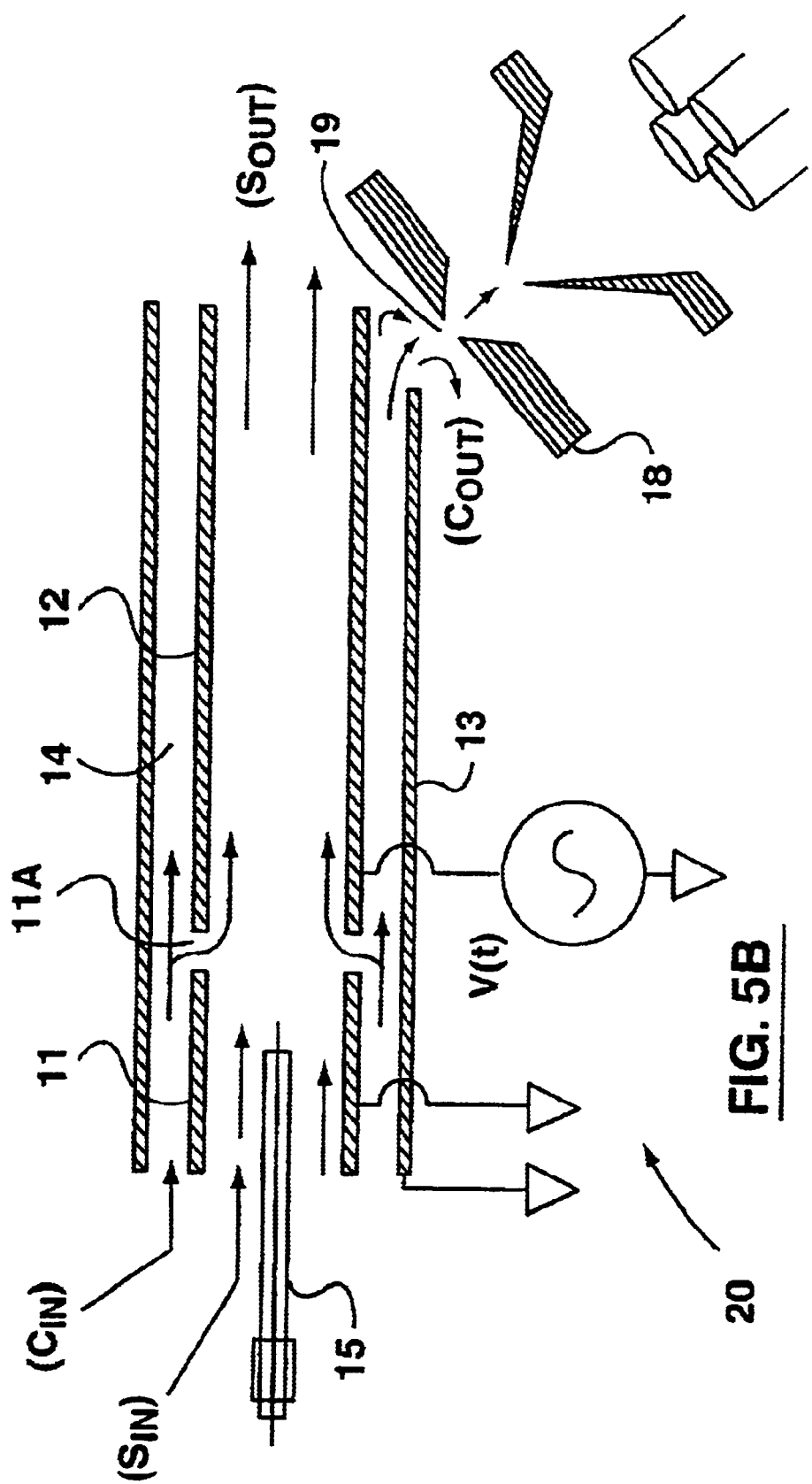

Referring to FIGS. 5A and 5B, the coupling of FAIMS and a mass spectrometer (FAIMS-MS 20) is shown schematically. The FAIMS-MS 20 of FIGS. 5A and 5B, and the FAIMS-E 10 shown in FIGS. 3A and 3B, differ significantly only at the detection end of the instrument. In accordance with the invention, the electrometer 17 has been replaced by a sampler cone 18, placed at the end of the FAIMS cylinders 12, 13 as is shown in a simplified form in FIG. 5B. The diameter of the orifice 19 in the sampler cone 18 is approximately 250 μm. The gas flows in the FAIMS-MS 20 are analogous to those in the FAIMS-E 10 except that the $C_{out}$ is divided into two components, namely the original $C_{out}$ and the flow through the orifice 19 into the mass spectrometer. The electrical waveforms applied to the long inner cylinder 12 are identical to those used in the FAIMS-E apparatus 10. The sampler cone 18 may be electrically insulated from the other components so a separate voltage OR can be applied to it. Furthermore, a voltage can be applied to the cylinders of the entire FAIMS unit ($V_{FAIMS}$) for the purpose of enhancing the sensitivity of the FAIMS-MS.

FIG. 5B shows the FAIMS cylinders 12, 13 at a 45 degree angle in relation to the sampler cone 18 of the mass spectrometer. FIG. 5A showed the FAIMS cylinders 12, 13 at a 90 degree angle in relation to the sampler cone 18. The way (i.e., the angle between the two tubes of the FAIMS and the sampler cone 18) in which the ions are extracted from the cylinders 12, 13 of the FAIMS-MS 20 into the mass spectrometer is not limited to these angles. Furthermore, the location in which the ions are extracted from the two tubes can also be changed. That is, the ions can be extracted anywhere along the separation region of the FAIMS.

Ion Focusing

Figure 6A:
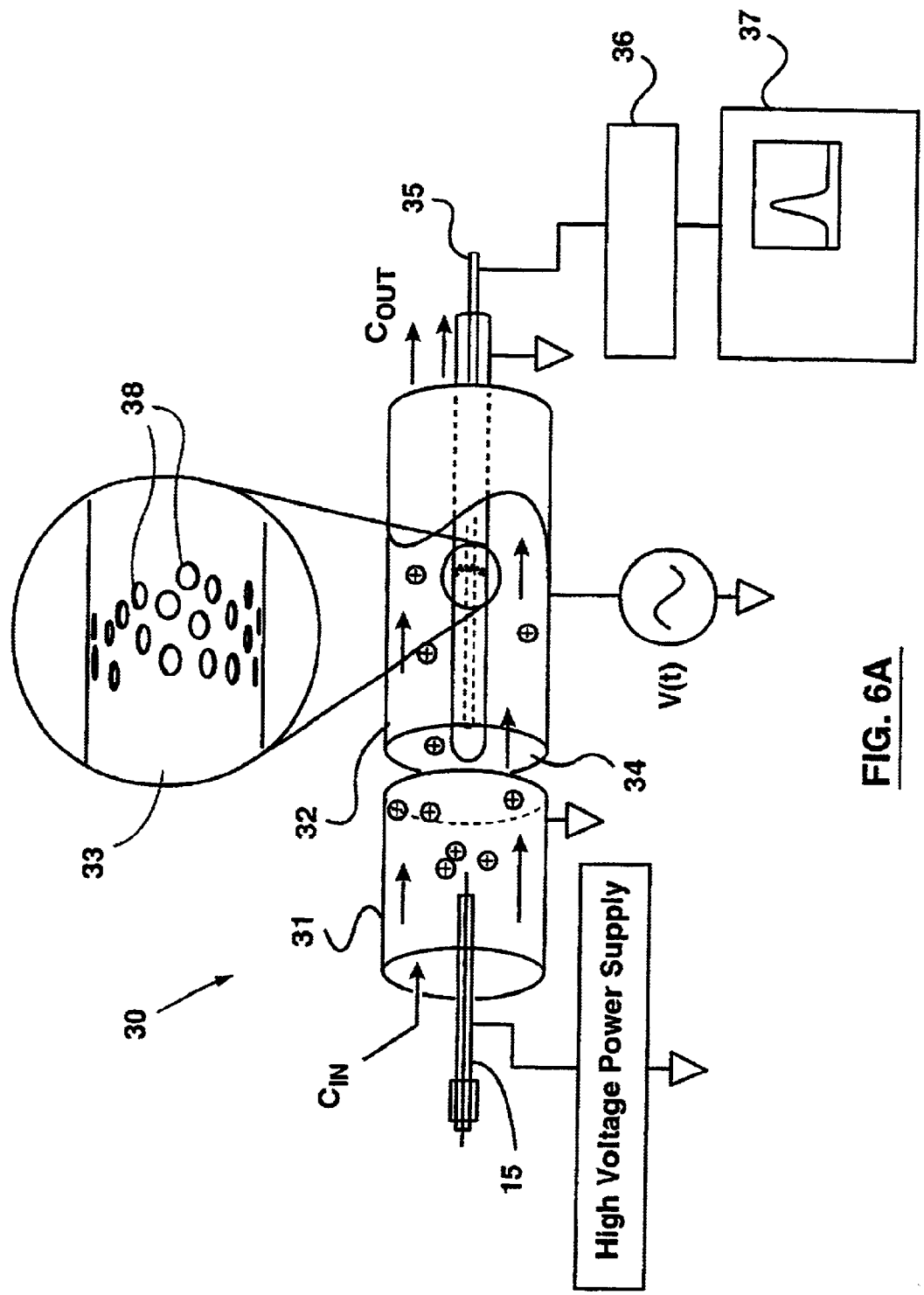
FIGS. 6A and 6B shows schematically a FAIMS apparatus for measuring the ion distribution in the analyzer region.
Figure 6B:
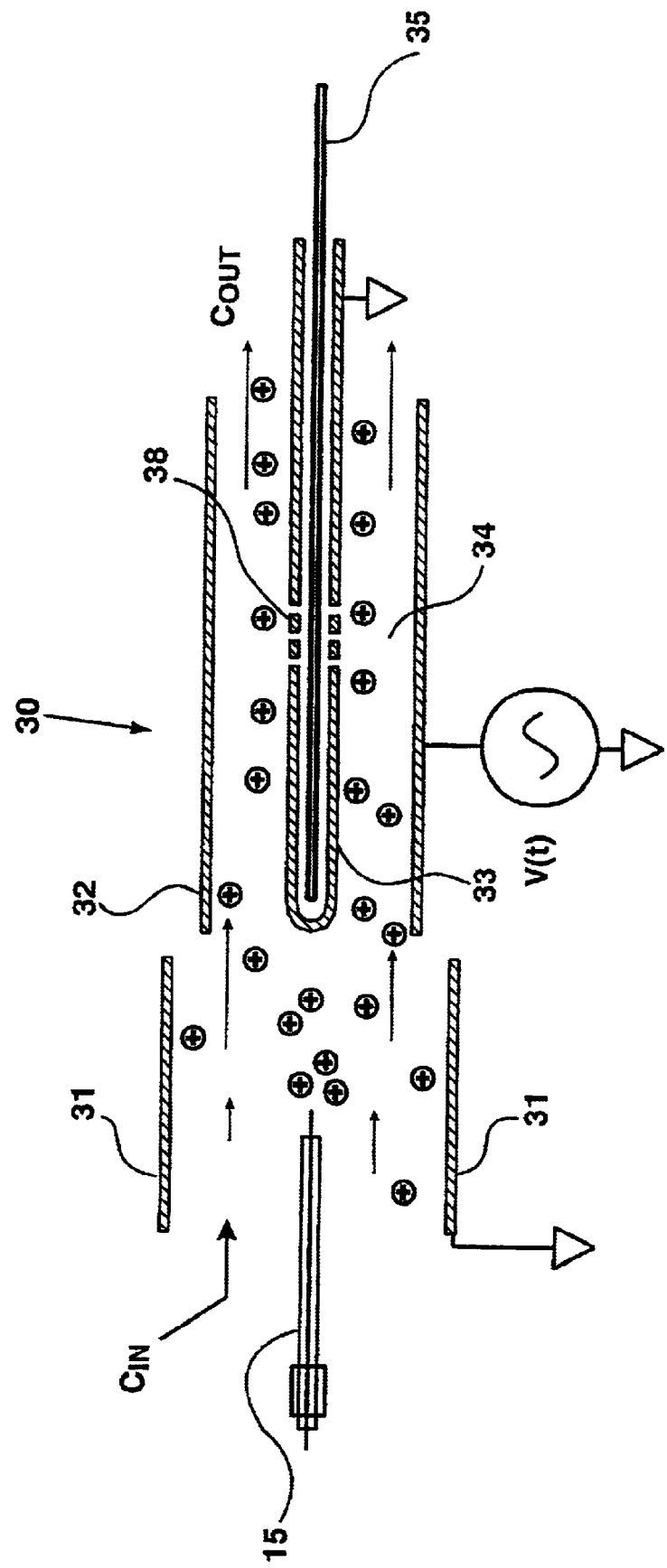

Referring now to FIGS. 6A and 6B, to demonstrate the focusing effect referred to above, a special FAIMS instrument was designed by the inventors and constructed to measure the ion distribution between the two cylinders (outer and inner cylinders) of a FAIMS device. This instrument will be referred to in this disclosure as the FAIMS-R1-prototype 30 and is illustrated schematically in FIGS. 6A and 6B. Ions were generated inside of an electrically grounded cylinder 31 approximately 35 mm long and 20 mm i.d. The tip of an ionization needle 15 was typically located near the center of this tube, and at least 15 mm from the end of the FAIMS analyzer region 34. The FAIMS analyzer region 34 in this embodiment is composed of an outer tube 32 which is 70 mm long and 6 mm i.d., and which surrounds a 2 mm o.d. inner shield electrode 33. The inner shield electrode 33 is an electrically grounded stainless steel tube which is closed at the end that faces the ionization needle 15. This inner electrode 33 surrounds, and shields, an electrically isolated conductor 35 passing into its center. This innermost conductor 35 (i.e. the ion collector electrode) is a collector for ions, and is connected to a fast current amplifier or electrometer 36 (e.g. Keithly model 428) and a digital storage oscilloscope 37 (e.g. LeCroy model 9450).

In the system shown in FIGS. 6A and 6B, the ions which surround the inner electrode 33 are forced inwards by a pulsed voltage. These ions travel from the FAIMS analyzer region 34 to the innermost conductor 35 through a series of 50 $\mu$m holes 38 drilled through the inner shield electrode 33. The holes drilled in the inner shield electrode 33 are positioned about 2 cm from the end facing the ionization needle 15, and are spaced about 0.5 mm apart for a distance of 10 mm on one side of the inner shield electrode 33. The holes 38 drilled in the inner shield electrode 33 are located in this manner to minimize the variability in distance between the inner shield electrode 33 and the outer cylinder 32 in the vicinity of these holes 38. It was the inventors' objective to measure the ion abundance radial profiles of the ions located in the annular space (i.e. the FAIMS analyzer region 34) between the inner shield electrode 33 and the outer electrode 32 by pulsing the ions toward the inner shield electrode 33 and through the holes 38 and against the innermost ion collector electrode 35. The time-dependent distribution of ions arriving at the innermost conductor 35 is related to the physical radial distribution of ions around the inner electrode 33. Excessive variation in the distance between the two cylinders 32, 33 would have increased the uncertainty of the ion arrival times at the innermost conductor 35, thus decreasing the spatial resolution of the measurements made with this device.

Figure 7:
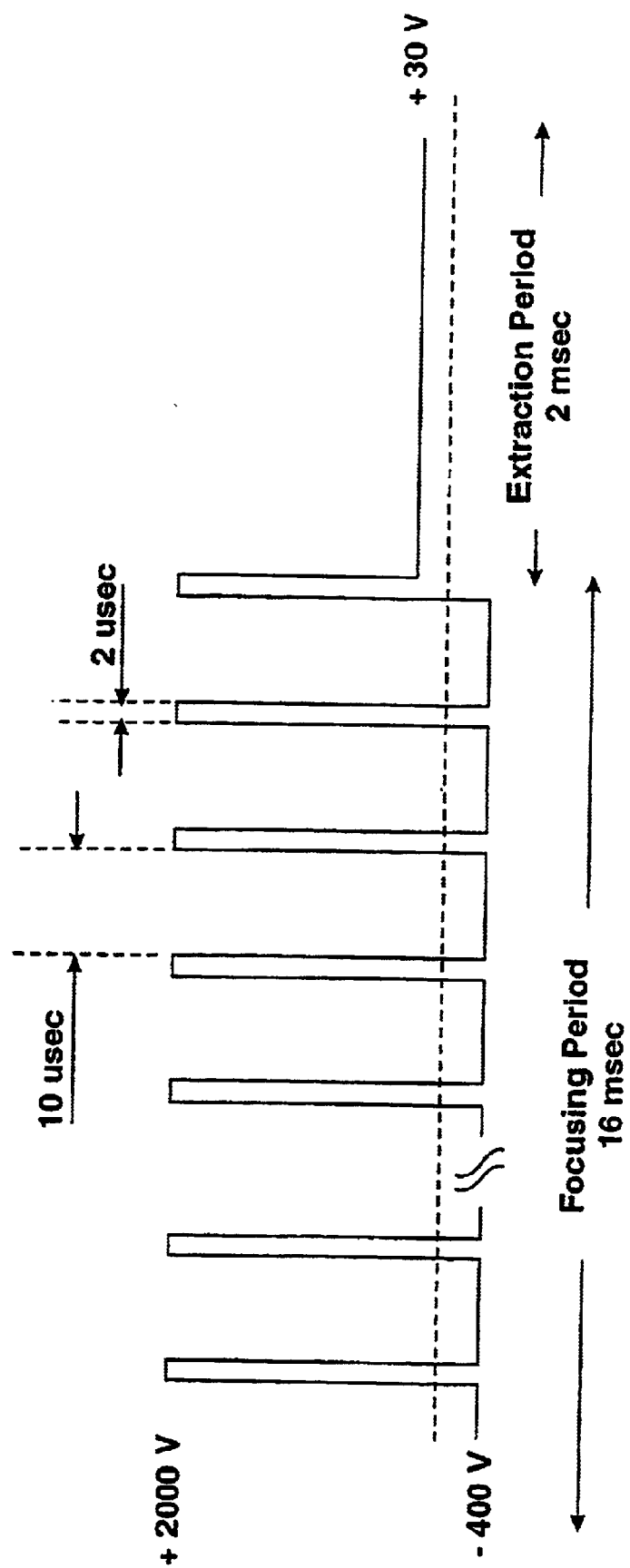
FIG. 7 illustrates the high voltage, high frequency asymmetric waveform applied to the FAIMS apparatus shown in FIGS. 6A and 6B.

Now referring to FIG. 7, the high voltage, high frequency asymmetric waveform V(t), applied to the FAIMS-R1-prototype of FIGS. 6A and 6B, is shown. The waveform is divided into two parts, the focusing period and the extraction period. The waveform was synthesized by an arbitrary waveform generator (e.g. Stanford Research Systems model DS340, not shown) and amplified by a pulse generator (e.g. Directed Energy Inc., model GRX-3.0K-H, not shown). The frequency of the waveform, and the relative duration of the high and low voltage portions of the waveform could easily be modified. Because of the high voltages, and steep rise-times of the square waves applied to this FAIMS-R1-prototype 30, the power consumption limits were severe, and waveforms in excess of about 1330 pulses (16 ms at 83,000 Hz) could not be delivered by this system without overheating electronic components of the high voltage pulse generator.

Note that, in the case of the FAIMS-R1-prototype 30, the high voltage, high frequency asymmetric waveform was applied to the outer cylinder 32 of the FAIMS-R1-prototype 30 shown in FIGS. 6A and 6B. Since all other forms of FAIMS discussed in this disclosure have the waveform applied to the inner tube or electrode, confusion may arise from the "polarity" of the waveform and the polarity of CV. In the FAIMS-R1-prototype 30 shown in FIGS. 6A and 6B, ions of type A (shown in FIG. 1) are focussed during application of the opposite polarity waveform and CV than that shown for the devices in FIGS. 3A, 3B, 5A and 5B. Nevertheless, for simplification, the polarity will be written to be the same as if the device was constructed in the same way as those of the more conventional configuration. In other words the ions transmitted during application of waveform #1 will appear with DV positive and with CV negative. (Please note, however, that the actual voltages used on the device in FIGS. 6A and 6B are DV negative and CV positive).

As was observed in the conventional parallel plate FAIMS apparatus described earlier (FIG. 2), the application of a high voltage asymmetric waveform V(t) will cause ions to migrate towards one of the FAIMS electrodes 2, 4 because of the changes in ion mobility at high electric fields (shown in FIGS. 1 and 2). This migration can be stopped by applying an electric field or compensation voltage CV in a direction to oppose the rigration. For the FAIMS-R1-prototype 30 of FIGS. 6A and 6B, this CV was applied to the same electrode as the high voltage asymmetric waveform (i.e. the outer electrode 32), and was added to the waveform as a small dc bias (up to ±50 V). At an appropriate combination of DV, and compensation voltage CV, a given ion will pass through the FAIMS device 30. The unit therefore acts like an ion filter. It is possible to fix conditions such that a single type of ion is isolated in the FAIMS analyzer 34 although a mixture flows uniformly out of the exit of the FAIMS device 30 although a mixture of ions are presented to the inlet of the FAIMS analyzer region 34.

The second part of the waveform shown in FIG. 7 (i.e. the extraction period) was used to pulse the ions out of the FAIMS analyzer region 34 between the outer electrode 32, and the inner shield electrode 33 (shown in FIGS. 6A and 6B). At the end of the focussing period, i.e. after 16 ms of waveform the asymmetric waveform was replaced by a constant dc bias of approximately +30 V. This caused the ions from the annular space 34 between the outer electrode 32 and the inner shield electrode 33 to move in the direction of the inner shield electrode 33. A detector bias of −5 V, applied to innermost ion collector electrode 35, helped to carry the ions from the vicinity of the holes 38 in the inner shield electrode 33, through the holes 38 and into contact with the innermost ion collector electrode 35. The +30 V bias created an electric field of approximately 150 V/cm across the FAIMS analyzer region 34 and most ions located within this region 34 travelled across the 2 mm space in about 1 ms. The ion current due to the arrival of ions at the center inner shield electrode 33 can be predicted. For example, if only one type of ion, with mobility of 2.3 cm$^2$/V-s, e.g., $(H_2O)_nH^+$ at ambient temperature and pressure conditions, was located in the FAIMS analyzer region 34, and if this ion was distributed evenly in the space, an approximately square-topped signal lasting approximately 0.6 ms should be observed. Deviation from this expected ion arrival profile would suggest that the ions were distributed in non-uniform profile across the FAIMS analyzer region 34 between the outer and inner cylinders of the FAIMS device 30.

Still referring to FIGS. 6A, 6B, and 7, the FAIMS-R1-prototype 30 was operated as follows. A 2 L/min flow of purified air, Carrier Gas In (Cin), was passed into the cylinder 31 housing the ionization needle 15. Approximately 2000 V was applied to the needle 15, and the voltage was adjusted to produce a stable ionization current. The high voltage asymmetric waveform V(t) was applied to the outer FAIMS cylinder 32 for approximately 16 ms; this was followed by a 2 ms extraction pulse (FIG. 7). The ion current striking the innermost ion collecting electrode 35 was detected and displayed on a digital oscilloscope 37. A measurement would typically consist of 100 averaged spectra, collected at a rate of approximately 5 Hz. Many experimental parameters were varied, including gas flow rates, the voltages of the asymmetric waveform V(t), the dc voltage applied to the outer electrode CV, and the extraction voltage.

Figure 8:
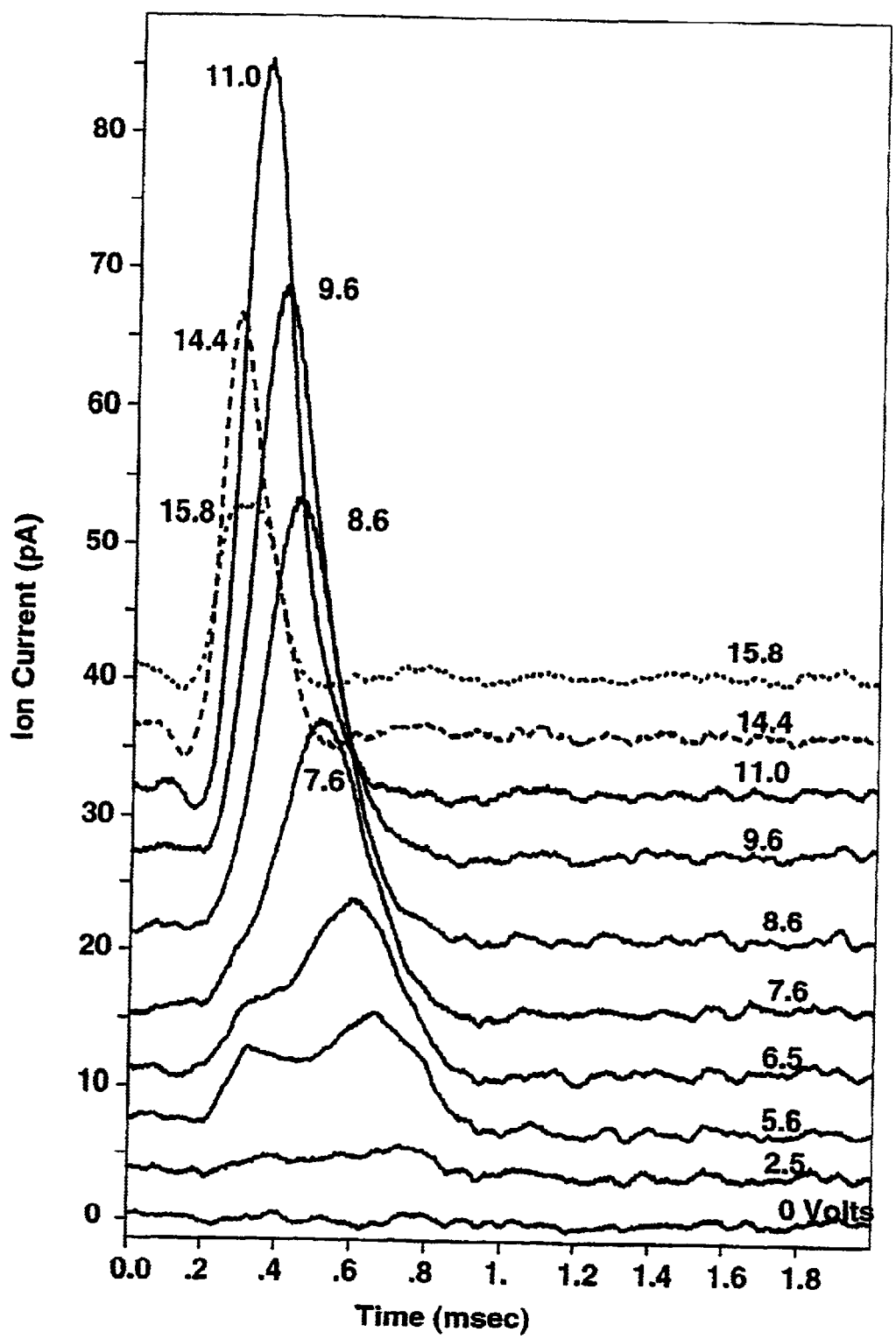
FIG. 8 illustrates varying ion arrival time profiles at he innermost ion collector electrode of the FAIMS apparatus in FIGS. 6A and 6B.

FIG. 8 illustrates the ion arrival times at the innermost ion collector electrode 35 observed by conducting these experiments. Each trace was recorded with 2500 V applied DV, but with variable CV voltages. As can be seen, during application of DV and CV, the radial distribution of ions is not uniform across the annular space of the FAIMS analyzer region 34. For example, at CV near −11 V, the ions are focussed into a narrow band near the inner electrode 33, and therefore are detected as a high intensity pulse occurring very early after the extraction voltage has been applied. At low CV, for example at −5.6 V, the ions are much more uniformly distributed between the walls of the concentric cylinders 32 33 making up the FAIMS analyzer region 34. When no electrical voltages are applied to the cylinders 32, 33, the radial distribution of ions should be approximately uniform across the FAIMS analyzer region 34 (data for this no-voltage experimental condition is not shown in this document). The experimental data shown in FIG. 8 is evidence that the ion focussing is indeed occurring in FAIMS instruments. This focussing results in the ions being focussed in a uniform "sheet" or band around the inner cylinder 33 within the FAIMS analyzer region 34. As mentioned previously, to the inventors' knowledge, this focussing effect has never been observed or explained previously.

Modes of Operation of FAIMS

The focussing and trapping of ions by the use of asymmetric waveforms has been discussed above. For completeness, the behaviour of those ions which are not focussed within the FAIMS analyzer region will be described here. As explained earlier, the ions which do not have the high field ion mobility properties suitable for focussing under a given set of DV, CV and geometric conditions will drift toward one or another wall of the device, as shown in FIG. 2. The rapidity with which they move to the wall depends on the degree to which their Kh/K ratio differs from that of the ion that might be focussed under the selected condition At the very extreme, ions of completely the wrong property i.e. type A ion versus type C ion shown in FIG. 1, will be lost to the walls very quickly.

The loss of ions should be considered one more way. If an ion of type A (FIG. 1) is focussed at DV 2500 volts, CV −11 volts in a given geometry (for example, the FAIMS-E device of FIGS. 3A–3B), is it reasonable to expect that the ion will also be focussed if the polarity of DV and CV are reversed, i.e. DV of −2500 volts and CV of +11 volts (both applied to the inner electrode). It would seem that the reversal of polarity is a trivial exercise and the ion should be focussed, however, this is not observed. Instead, the reversal of polarity in this manner creates the mirror image effect of the ion focussing behaviour of FAIMS. The result of such polarity reversal is that the ions are not focussed, but rather are extremely rapidly rejected from the device, and collide with the walls of the cylinders 12, 13. The mirror image of a trapping valley, is a hill-shaped potential surface. The ions will slide to the center of the bottom of a trapping potential valley (2 or 3-dimensions), but will slide off of the top of a hill-shaped surface, and hit the wall of an electrode. This apparently anomalous behaviour is a consequence of the cylindrical geometry of the FAIMS-E.

This is the reason for the existence, in the FAIMS, of the independent "modes" called 1 and 2. In this disclosure, the FAIMS instrument is operated in four modes: P1, P2, N1, and N2. The "P" and "N" describe the ion polarity, positive (P) and negative (N). The waveform (FIG. 4, wave #1) with positive DV (where DV describes the peak voltage of the high voltage portion of the asymmetric waveform) yields spectra of type P1 and N2, whereas the reversed polarity (FIG. 4, wave #2, negative DV) waveform yields P2 and N1. The discussion thus far has considered positive ions but, in general, the same principles can be applied to the negative ions, as explained in the preliminary note to the Detailed Description.

Separation Experiments

Based on the FAIMS principles discussed above and the experiments conducted by the inventors to demonstrate the concept of ion focussing, the inventors have developed what is believed to be a previously unknown method for separation of isotopes in the gaseous phase, at atmospheric pressure and room temperature. Ion separation experiments involving chlorine ions are provided by way of example.

Chlorine Isotope Separation

Isotope tracer studies and internal standardization using enriched chlorine isotopes have gained widespread acceptance in both environmental and biomedical arenas. Dioxins and polychlorobiphenyls (PCB's) are two classes of environmental contaminants containing chlorine that have attracted intense scrutiny for a long time. Analysis procedures generally include liquid or solid phase extraction combined with gas chromatography using mass spectrometric detection. Inherent to all of these analytical procedures is the need for proper internal standardization to evaluate extraction efficiencies and ensure accurate quantitation at trace levels. Synthesis of isotopically labelled internal standards relies on the availability of a reliable source of high purity isotopes. Incorporation of such internal standards to routine analysis depends on the quality of analytical data required and the availability and cost of chemical standards.

Currently there are very few methods capable of chlorine isotope separation and/or enrichment at atmospheric pressure, even fewer (if any) are viable from an economic standpoint. A testament to this fact is the recent shutdown of a federally subsidized enriched isotope production laboratory in the United States. Unfavourable cost analysis, rather than a lack of demand was the apparent cause for the halt in production. Since the shutdown, the price of existing stocks of enriched chlorine isotopes and chlorine labelled compounds has risen dramatically.

Other studies in the prior art have reported isotopic fractionation using separation techniques such as liquid chromatography and capillary zone electrophoresis (CZE). It has been reported that near baseline separation of chloride isotopes has been achieved using CZE by carefully adjusting the electroosmotic flow to be equal but opposite to the electrophoretic migration of chloride ions. Despite the impressive results of these studies, it is unlikely that CZE will gain widespread use for isotope separation because of the degree of development of the method required, inherently poor reproducibility, transient nature of the analyte signal, and the poor specificity and selectivity of detection techniques generally associated with CZE. In short, the feasibility of isotope enrichment by CZE is not an issue due to the very low sample capacity.

The present invention was developed to address some of the limitations in the prior art identified above for separating and enriching isotopes. In the present example, the application of the method of the present invention to separate and enrich the isotopes of chlorine is shown and described. The method described is designed to separate and enrich isotopes without the need for expensive equipment, intensive method development, or complicated sample preparation.

Referring back to FIGS. 5A and 5B, an ESI-FAIMS interface was coupled to a PE Sciex API 300 triple quadrupole mass spectrometer. The outer cylinder 13 and the shorter inner cylinder 11 of the FAIMS instrument were held at the same electrical potential (e.g., 0 V). The longer inner cylinder 12 had the high frequency (210 kHz), high voltage (up to 4950 V p-p), asymmetric waveform (FIG. 4(b)) applied to it, thereby establishing the electric field between the long inner cylinder 12 and outer cylinder 13. In addition to this high frequency waveform, the CV was also applied to the long inner cylinder 12.

Still referring to FIGS. 5A and 5B, the electrospray needle 15 was placed on the centre axis of the shorter inner cylinder 11, terminating about 5 mm short of the gap 11A between the two inner cylinders 11, 12. The electrospray ions were driven radially outward by the electric field to the analyzer region 14 through the 5 mm gap 11A between the two inner cylinders 11, 12. For the generation of chloride ions, the electrospray needle 15 was held at −1950 V, giving a current of roughly −45 nA.

Gas connections to the FAIMS analyzer are also shown in FIG. 5B. Compressed air was passed through a gas purification cylinder (charcoal/molecular sieve) and introduced into the FAIMS analyzer. Gas entered through the carrier in ($C_{in}$) port, and exited via the carrier out ($C_{out}$) and sample out ($S_{out}$) ports. For the experiments, the gas was introduced through $C_{in}$ at a flow rate of 5 L/min. The gas exited through $S_{out}$ at 1 L/min and through $C_{out}$ at 4 L/min. A fraction of $C_{in}$, directed radially inward through the 5 mm gap 11A between the inner cylinders 11, 12 acted as a curtain gas. While the ions formed by ESI were driven radially outward through the gap 11A by the electric field, the curtain gas prevented neutrals from entering the analyzer region 14. The curtain gas portion of $C_{in}$, along with the neutrals, exited the FAIMS analyzer via the $S_{out}$ port. The remainder of the gas flow carried the electrospray ions along the length of the analyzer region 14 between the outer cylinder 13 and the long inner cylinder 12.

If the combination of DV and CV were appropriate, ions were transferred to the vacuum chamber of the mass spectrometer (FAIMS-MS) through the orifice 19 of the sampler cone 18. The diameter of the orifice 19 in the sampler cone 18 was approximately 270 $\mu$m. The orifice 19 was electrically insulated from the FAIMS analyzer and a separate voltage (OR) of −24 V was applied to it. An offset voltage of 49 V was applied to the entire FAIMS analyzer ($V_{FAIMS}$) to enhance the sensitivity of the FAIMS-MS 20. The skimmer cone 18A was held at ground potential and the small ring electrode normally located behind the orifice 19 (not shown) was not incorporated into the present interface, resulting in a significant loss of sensitivity for the low mass chloride ions. The pressure inside the FAIMS analyzer was kept at roughly 770 torr.

A 1 mL stock solution containing 0.0097 grams of reagent grade ammonium chloride (MW 53.49, Anachemia) was prepared in HPLC grade methanol (Anachemia). A 2 $\mu$L aliquot of this stock solution was then diluted in 2 mL of methanolic ESI buffer containing 15 $\mu$M ethylenediaminetetraacetic acid (EDTA), (MW 292.25, Fisher Scientific) to give a sample solution containing 180 $\mu$M of chloride. An EDTA based electrospray buffer was chosen to improve the yield of free chloride ions in the gas phase. This is accomplished by preferentially binding most metal ions, $M^{n+}$, thus preventing the formation of various metal-chloride species in solution, $MCl_n^-$.

Figure 9:
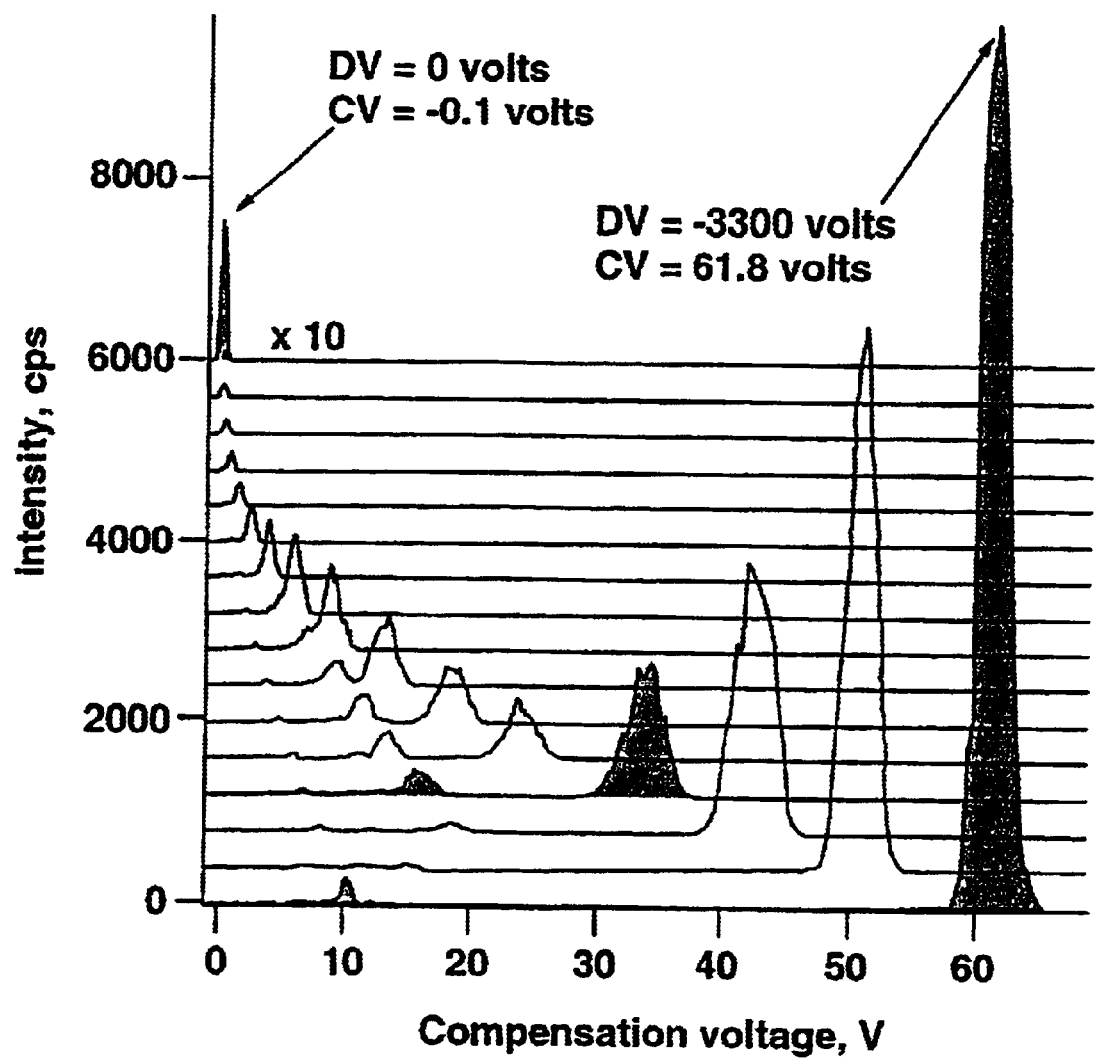
FIG. 9 shows a series of 16 ion selected compensation voltage (IS-CV) spectra for a sample solution containing ammonium chloride and EDTA at various DV values.

Now referring to FIG. 9, the capability of the FAIMS analyzer to transmit (with focusing) chloride ions generated from an ESI source is demonstrated. Each trace in FIG. 9 represents an ion-selected CV spectrum (IS-CV spectrum), collected at regular intervals of DV by scanning the CV from −1 to 69 volts, while monitoring a mass to charge ratio (m/z) of −35. The dwell time and number of scans were kept constant for each spectrum The plot consists of a total of 16 IS-CV spectra, the first spectrum (top trace) was acquired with a dispersion voltage, DV, of 0 volts (i.e. FAIMS was "disabled"). The signal intensity has been multiplied by a factor of 10 for presentation purposes. The next IS-CV spectrum was acquired at DV=−500 V, and subsequent spectra acquired after increasing the magnitude of DV by 200 V to a maximum of −3000 V. The final spectrum in the series was acquired at DV=−3300 volts. From this series of spectra, there are four things to note as the magnitude of DV is increased: (1) the peaks shift to higher compensation voltages; (2) the peak widths vary; (3) the ion current separates into several IS-CV peaks; and (4) the total ion current increases substantially. Three of the spectra included in FIG. 9 (DV=0, −2700, and −3300 volts) have been flagged for further discussion by shading to baseline.

Figure 10A:
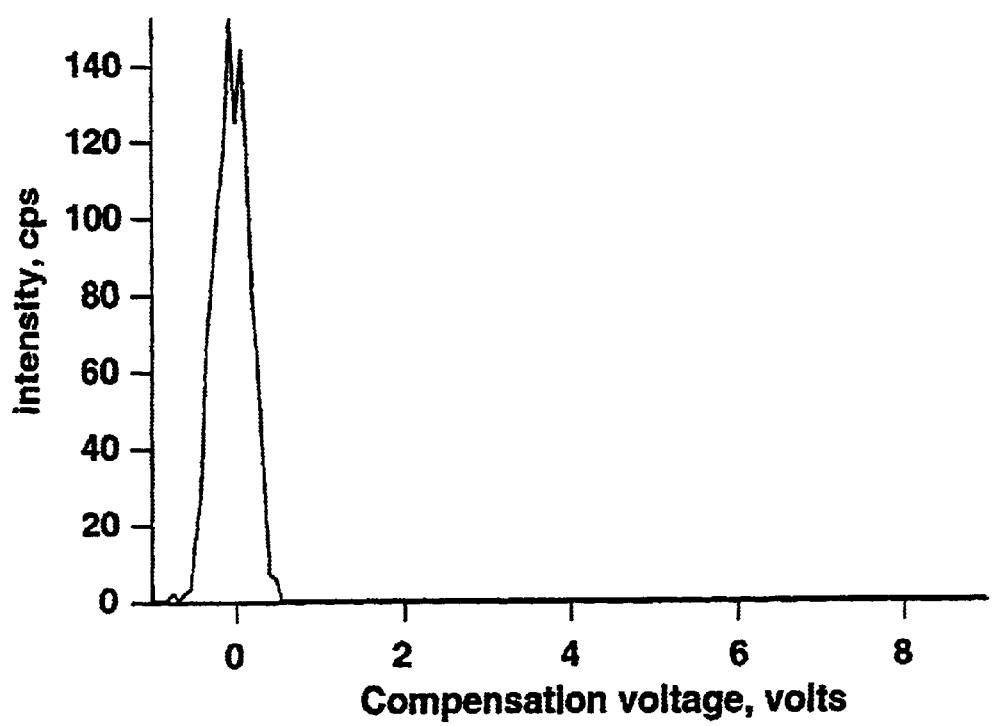
FIG. 10A shows an expanded IS-CV spectrum of the sample solution used in FIG. 9 at DV=0 volts.
Figure 10B:
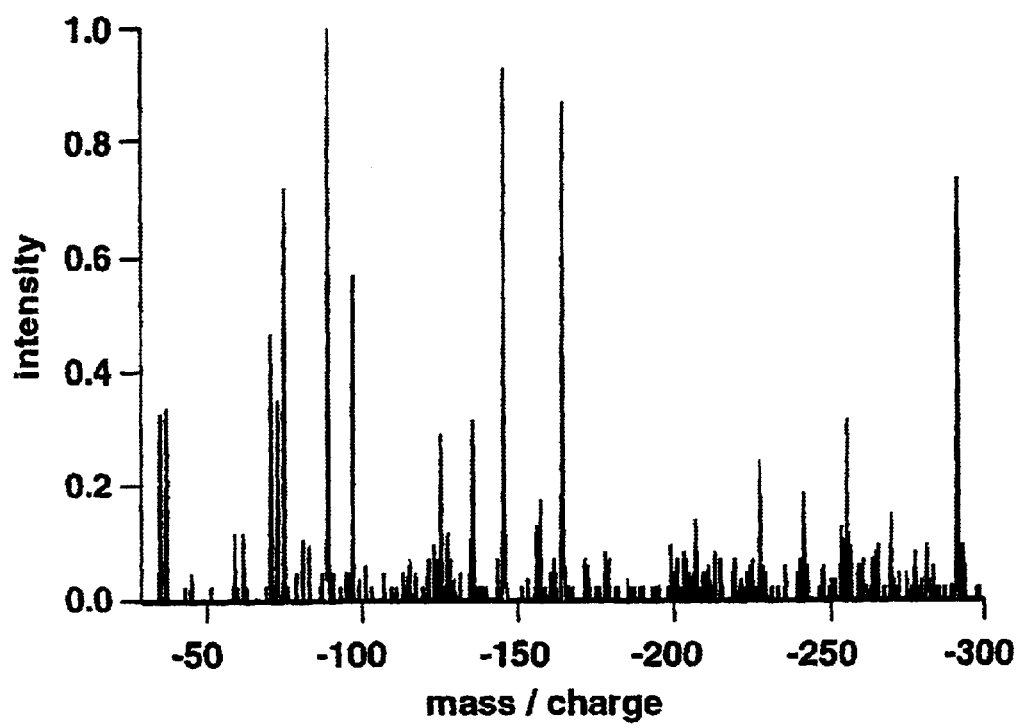
FIG. 10B shows a mass spectrum for the sample solution used in FIG. 9 at DV=0 volts and CV=0 volts.

Now referring to FIG. 10A, the IS-CV spectrum acquired at DV=0 volts (i.e. with FAIMS disabled) is shown. Since there is no applied electric field, there is no net ion motion toward either electrode within the FAIMS analyzer so the peak appears at CV ~0 volts. A mass spectrum acquired by setting CV=0 volts is shown in FIG. 10B. Most of the major ions in the spectrum are easily identifiable, a detailed list is given in Table 1 (FIG. 10C). Note that most of the ions above m/z −140 are related to EDTA. This ESI-FAIMS-MS spectrum with FAIMS disabled is very similar to a conventional ESI-MS spectrum.

Figure 11A:
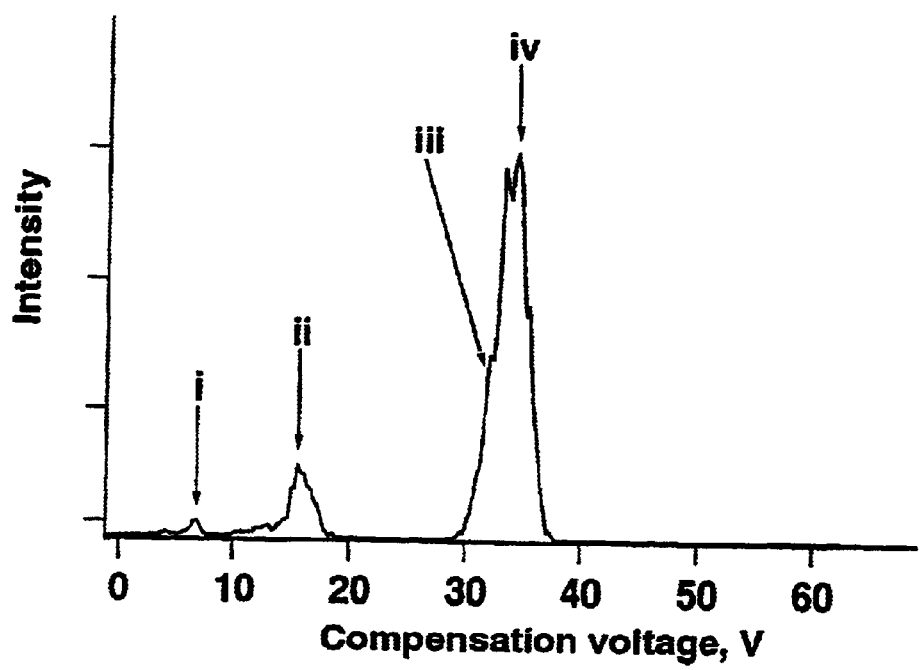
FIG. 11A shows an IS-CV spectrum for the solution used in FIG. 9 at DV=−2700 volts.
Figure 11B:
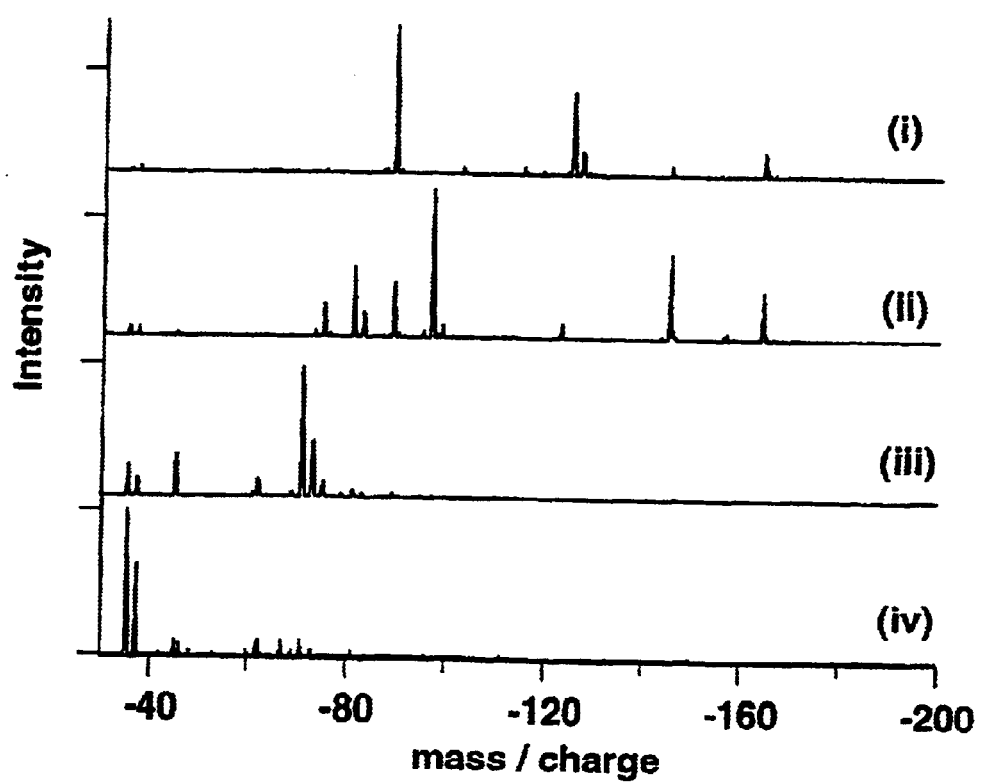
FIG. 11B shows mass spectra for the solution used in FIG. 9 at DV=−2700 volts and at various CV values.

Now referring to FIG. 11A, the IS-CV spectrum acquired at DV=−2700 volts is shown. From the IS-CV spectra, it is observed that three distinct ions or chemical entities are transmitted through the FAIMS analyzer and yield an ion of m/z −35. Based on earlier studies conducted by the inventors, it was expected that one of the peaks would correspond to free chloride ion while the others represent adducts that dissociate via collision induced dissociation in the FAIMS-MS interface to yield bare chloride ion. Identification of the source of these peaks was undertaken by sequentially tuning the CV to each IS-CV peak maximum and collecting mass spectra. Mass spectra collected at the same MS conditions as used for the IS-CV spectrum in FIG. 11A are shown in FIG. 11B, traces (i) through (iv). Given the resolution of FAIMS, some mass spectral overlap is inevitable; therefore, not all ions in the MS scans of FIG. 11B are related to chloride. The majority of the ions identified from the spectrum in FIG. 10B and listed in Table 1 (FIG. 10C) will appear at some value of CV between 0 and 40 volts with DV=−2700 V. All four mass spectra in FIG. 11B show the presence of some $^{35}Cl^-$ ion. The first three spectra, FIG. 11B traces (i) to (iii), also exhibit characteristic chloride isotope patterns at higher masses. In FIG. 11B trace (i), CV=6.7 volts, a chloride adduct to oxalic acid ($H_2C_2O_4$) is identified at m/z −125 and −127. Note that in addition to the chloride related species transmitted at CV=6.7 volts, other chemical species also appear in the mass spectrum because they have similar $K_h/K$ properties, such species include $K(HEDTA)^{2-}$ at m/z −164. The oxalate ion (m/z −89) in this spectrum is formed from the dissociation of the chloride/oxalic acid adduct species. In FIG. 11B trace (ii), CV=15.5 volts, another adduct of chloride is identified, in this case chloride is associated with formic acid ($H_2CO_2$). FIG. 11B trace (iii) was collected on the shoulder of the major peak in FIG. 11A, CV=32.0 volts. In this case, a species containing two chloride ions is identified as a hydrochloric acid adduct, $HCl_2^-$ (m/z −71). Finally, collection of a mass spectrum at the maximum of the peak at CV=34.5 volts, yields a spectrum that indicates the presence of free chloride ion (FIG. 11B trace (iv)). There are several other ions with similar $K_h/K$ behaviour as chloride at DV=−2700 volts, including nitrite ($NO_2^-$) and nitrate ($NO_3^-$), hence they also appear in the mass spectrum. In addition, there are peaks in this spectrum relating to solvated chloride species, i.e. $Cl(H_2O)^-$ (m/z −53) and $Cl(CH_3OH)^-$ (m/z −67). These solvated species are likely a post-FAIMS phenomenon, generated by the recombination of chloride with solvent vapour, within the jet expansion region of the mass spectrometer.

Figure 12:
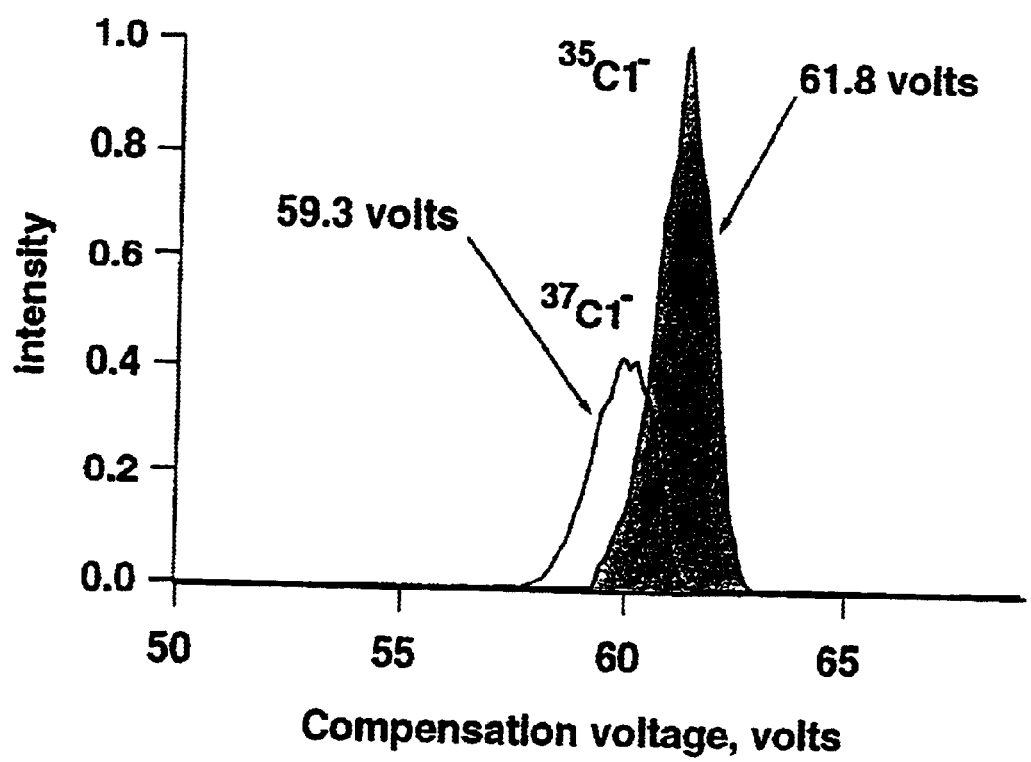
FIG. 12 shows an expanded IS-CV spectra of the solution used in FIG. 9 at DV=−3300 volts.

Next, FIG. 12 shows the final IS-CV spectrum flagged from FIG. 9 (at DV=−3300 volts) and plotted over a CV range of 50 to 69 volts. The $^{37}Cl$ isotope is included in this figure to demonstrate the capability of FAIMS for the separation of isotopes. There are some points to be emphasised pertaining to the results in FIG. 12. First, it is seen that the heavier chlorine isotope, $^{37}Cl$, appears at lower compensation voltage. This is consistent with the inventors' previous findings for type A ions (low mass, increasing mobility with electric field) that CV is inversely dependent on ion mass within series of ions with homologous structures. Secondly, the accuracy of the isotope ratio determined from this figure appears to be relatively poor. However, it is speculated that this is a post FAIMS effect brought about in the MS. Third, the two CV peaks are not symmetric, and in fact there appears to be some "tailing" for both ions to the low CV side. This peak asymmetry appears to be an artifact of the 45 degree ion extraction from FAIMS into the mass spectrometer used in this experiment. Finally, comparison of the measured ion current between the first (DV=0 volts) and last (DV=−3300 volts) yields a 75-fold increase in sensitivity as a result of a two-dimensional ion focusing mechanism that occurs within the FAIMS analyzer.

Figures 13A, 13B, 13C:
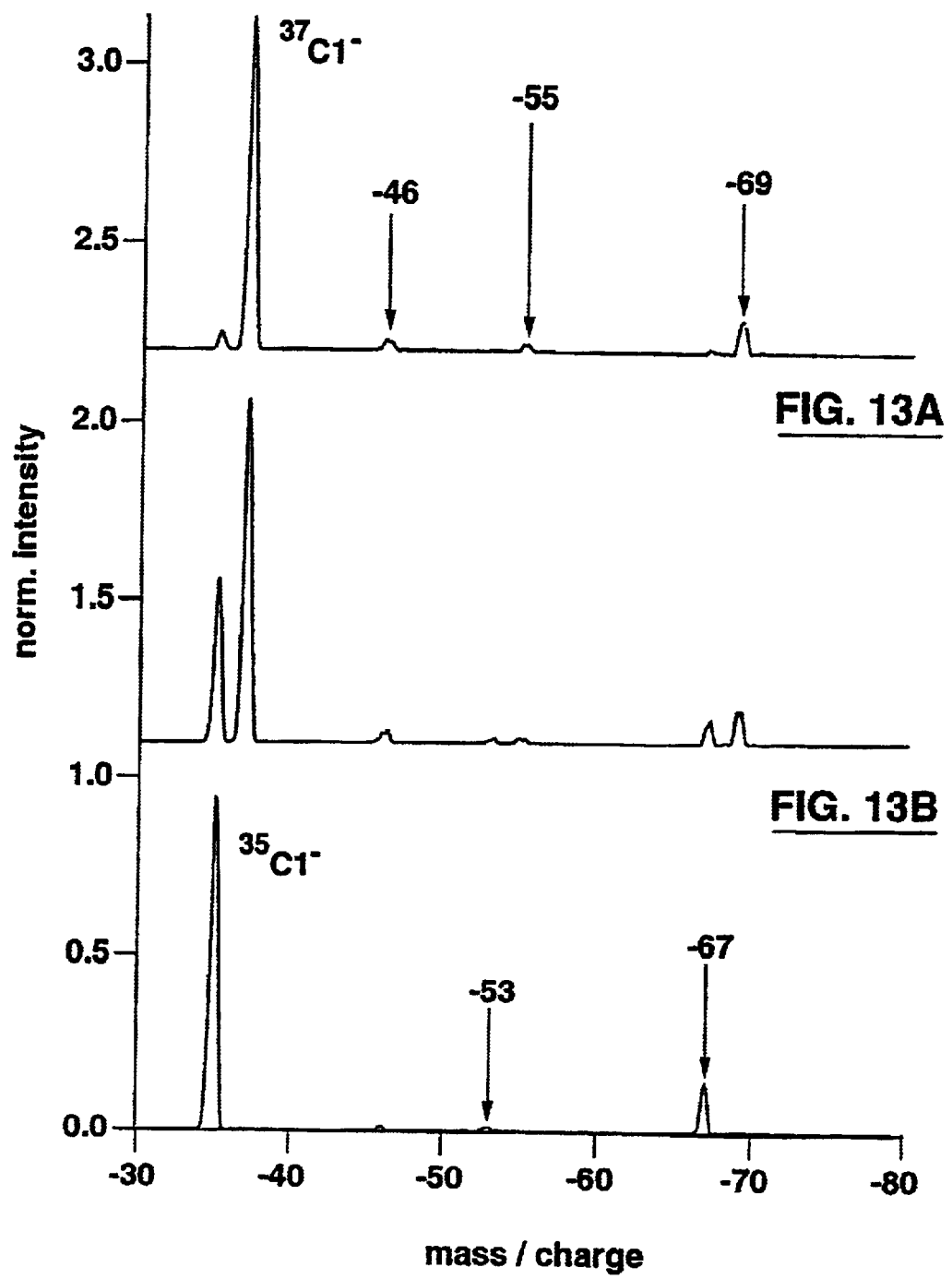
FIGS. 13A–13C show mass spectra of the solution used in FIG. 9 at DV=−3300 volts and at various CV values.

Finally, referring to FIGS. 13A–13C, mass spectra collected at CV values of 59.3, 60.0 and 61.8 volts respectively, with DV held constant at −3300 volts are shown. From these spectra, it is shown that the FAIMS analyzer is able to separate the two isotopes on a continuous basis. In addition to the bare chloride ions at m/z values of −35 and −37, the spectra also contain signal from nitrite anion (m/z −46) and two solvated chloride species, $Cl(H_2O)^-$ and $Cl(CH_3OH)^-$, at m/z values of −53, −55, −67 and −69.

Although the invention has been described and illustrated with reference to specific embodiments, those skilled in the art will recognize that the invention may be otherwise embodied within the scope of the following claims. Specifically, while the use of a mass spectrometer for measuring ions transmitted through a FAIMS analyzer is shown and described, it will be understood that a mass spectrometer is not required in order for separation of isotopes to occur. Once the operating conditions for the FAIMS analyzer have been established, the desired isotopes being transmitted through the FAIMS analyzer may be collected rather than being passed into a mass spectrometer for further analysis.

We claim:

1. A method for enriching and/or identifying isotopes, comprising:
   a) providing at least one ionization source for providing ions including two isotopes of a same element;
   b) providing an analyzer region defined by a space between at least first and second spaced apart electrodes, said analyzer region being in communication with at least one of each of a gas inlet, a gas outlet, an ion inlet and an ion outlet, and introducing said ions into said analyzer region through said ion inlet;
   c) applying an asymmetric waveform voltage and a direct current compensation voltage to at least one of said electrodes;
   d) setting said asymmetric waveform voltage in order to effect a difference in net displacement between said isotopes in the time of one cycle of said applied asymmetric waveform voltage;
   e) varying said direct current compensation voltage to compensate for some of the displacement of said isotopes resulting from the applied asymmetric waveform voltage and measuring resulting transmitted ions at said ion outlet, so as to produce a compensation voltage scan for said transmitted ions;
   f) identifying peaks in said compensation voltage scan corresponding to said isotopes; and,
   g) setting said direct current compensation voltage to correspond to one of said peaks, so as to separate and enrich one of said two isotopes.

2. The method claimed in claim 1, which includes operating substantially at atmospheric pressure and substantially at room temperature.

3. The method claimed in claim 2, which includes detecting said transmitted ions by mass spectrometry.

4. The method claimed in claim 1, which includes generating said ions for said source of ions by electrospray ionization.

5. The method claimed in claim 4, which includes detecting said transmitted ions by mass spectrometry.

6. The method claimed in claim 1, which includes detecting said transmitted ions by mass spectrometry.

7. The method claimed in claim 6, which includes subjecting the transmitted ions to a mass analysis scan to provide ion intensity data over a selected range of mass to charge ratios.

8. The method claimed in claim 1, which includes providing a gas flow through said analyzer region, so as to transport said ions along said analyzer region.

9. The method claimed in claim 1, which includes collecting the desired one of said two isotopes for further processing.

10. A method for enriching and/or identifying ions of differing isotopic composition, comprising:
    a) providing at least one ionization source for producing ions including two ions of differing isotopic composition;

b) providing an analyzer region defined by a space between at least first and second spaced apart electrodes, said analyzer region being in communication with at least one of each of a gas inlet, a gas outlet, an ion inlet and an ion outlet, and introducing said ions into said analyzer region through said ion inlet;

c) applying an asymmetric waveform voltage and a direct current compensation voltage to at least one of said electrodes;

d) setting said asymmetric waveform voltage in order to effect a difference in net displacement between said two ions of differing isotopic composition in the time of one cycle of said applied asymmetric waveform voltage; and, e) setting said direct current compensation voltage to a determined value to separate and enrich only one of said two ions of differing isotopic composition.

11. The method claimed in claim 10, which includes operating substantially at atmospheric pressure and substantially at room temperature.

12. The method claimed in claim 10, wherein, said ions introduced into said ion inlet are produced by electrospray ionization.

13. The method claimed in claim 10, which includes detecting said transmitted ions by mass spectrometry.

14. The method claimed in claim 13, which includes subjecting the transmitted ions to a mass analysis scan to provide ion intensity data over a selected range of mass to charge ratios.

15. The method claimed in claim 10, which includes providing a gas flow through said analyzer region, so as to transport said ions along said analyzer region.

16. The method claimed in claim 10, which includes collecting the desired one of said two ions of differing isotopic composition for further processing.

17. The method claimed in claim 10, including prior to setting said direct current compensation voltage to a determined value:

d1) varying said direct current compensation voltage to compensate for some of the displacement of one of said ions of differing isotopic composition resulting from the applied asymmetric waveform voltage and measuring resulting transmitted ions at said ion outlet, so as to produce a compensation voltage scan for said transmitted ions of different isotopic composition; and, d2) identifying peaks in said compensation voltage scan corresponding to said ions of different isotopic composition.

* * * * *